US012091602B2

(12) United States Patent
Shanks et al.

(10) Patent No.: US 12,091,602 B2
(45) Date of Patent: Sep. 17, 2024

(54) HETEROARYL-THIO-SUBSTITUTED PYRONES

(71) Applicant: Iowa State University Research Foundation, Inc., Ames, IA (US)

(72) Inventors: Brent Shanks, Ames, IA (US); George A. Kraus, Ames, IA (US); William Bradley, Schaumburg, IL (US); Jiajie Huo, Boulder, CO (US); Kyle Podolak, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 312 days.

(21) Appl. No.: 17/504,307

(22) Filed: Oct. 18, 2021

(65) Prior Publication Data

US 2022/0119709 A1    Apr. 21, 2022

Related U.S. Application Data

(60) Provisional application No. 63/094,579, filed on Oct. 21, 2020.

(51) Int. Cl.
| | | |
|---|---|---|
| C09K 15/30 | (2006.01) |
| C07D 213/70 | (2006.01) |
| C07D 233/84 | (2006.01) |
| C07D 235/28 | (2006.01) |
| C07D 249/12 | (2006.01) |
| C07D 277/36 | (2006.01) |
| C07D 285/125 | (2006.01) |
| C07D 405/12 | (2006.01) |
| C07D 409/12 | (2006.01) |
| C07D 417/12 | (2006.01) |
| C09D 5/08 | (2006.01) |

(52) U.S. Cl.
CPC ............ C09K 15/30 (2013.01); C07D 213/70 (2013.01); C07D 233/84 (2013.01); C07D 235/28 (2013.01); C07D 249/12 (2013.01); C07D 277/36 (2013.01); C07D 285/125 (2013.01); C07D 405/12 (2013.01); C07D 409/12 (2013.01); C07D 417/12 (2013.01); C09D 5/086 (2013.01)

(58) Field of Classification Search
CPC ..... C09K 15/30; C07D 405/12; C07D 417/12
See application file for complete search history.

(56) References Cited

PUBLICATIONS

STN Reg No. 353260-96-5, entered into STN on Aug. 28, 2001. (Year: 2001).*
Mostardeiro et al, Efficient synthesis of 4-sulfanylcoumarins from 3-bromo-coumarins via a highly selective DABCO-mediated one-pot thia-Michael addition/elimination process, Jan. 2020, RSC adv., vol. 10, p. 482-491 (Year: 2020).*
STN Reg No. 353260-94-3, entered into STN on Aug. 28, 2001 (Year: 2001).*
STN Reg No. 353260-91-0, entered into STN on Aug. 28, 2001 (Year: 2001).*
Balalas, T., "Pd-Catalyzed Efficient Synthesis of Azacoumestans via Intramolecular Cross Coupling of 4-(Arylamino)coumarins in the Presence of Copper Acetate under Microwave", Synthesis-Stuttgart, 49(11), (2017), 2575-2583.
Bradley, William, "Developing Green Processes for the Conversion of Biobased Materials into Pyrones", Dissertation, Iowa State University, (2019), 89 pgs.
Finsgar, Matjaz, "Application of corrosion inhibitors for steels in acidic media for the oil and gas industry: A review", Corrosion Science, 86, (Sep. 2014), 17-41.
Loganayagi, C., "Opuntiol: An Active Principle of Opuntia elatior as an Eco-Friendly Inhibitor of Corrosion of Mild Steel in Acid Medium", ACS Sustainable Chemistry and Engineering, pubs.acs.org journal ascecg, ACS PublicationsResearch Article, 2014 American Chemical Society, (2014), 606-613.

* cited by examiner

*Primary Examiner* — Kamal A Saeed
*Assistant Examiner* — Karen Cheng
(74) *Attorney, Agent, or Firm* — Schwegman Lundberg & Woessner, P.A.

(57) ABSTRACT

A heteroaryl-thio-substituted pyrone compound that is a heteroaryl-thio-substituted pyrone or a heteroaryl-thio-substituted coumarin. In various embodiments, the heteroaryl-thio-substituted pyrone compound or a reaction product thereof is a metal corrosion inhibitor.

9 Claims, 9 Drawing Sheets

HETEROARYL-THIO-SUBSTITUTED PYRONES

CROSS-REFERENCE TO RELATED APPLICATION

This application claims the benefit of priority to U.S. Provisional Patent Application Ser. No. 63/094,579 filed Oct. 21, 2020, the disclosure of which is incorporated herein in its entirety by reference.

STATEMENT OF GOVERNMENT SUPPORT

This invention was made with Government support under Contract No. DE-EE0008492 awarded by the Department of Energy. The U.S. Government has certain rights in this invention.

BACKGROUND

Corrosion inhibitors are additives that decrease the rate of corrosion of a metal or an alloy. For example, in a number of water pipes, small amounts of acid corrode pipes over time. These acids corrode the pipes and can deposit iron oxides or rust, lowering stability of the alloy. In oil fields a number of iron pipes corrode and become damaged over time due to a minor amount of acid in the facility.

Although some examples of organic corrosion inhibitors exist, such as hexamethylenetetramine (HTMA, also known as urotropin), other organic corrosion inhibitors are needed that have equal or greater corrosion inhibiting activity.

SUMMARY OF THE INVENTION

The present invention provides a heteroaryl-thio-substituted pyrone compound that is a heteroaryl-thio-substituted pyrone or a heteroaryl-thio-substituted coumarin.

The present invention provides a corrosion inhibition composition that includes the heteroaryl-thio-substituted pyrone compound that is a heteroaryl-thio-substituted pyrone or a heteroaryl-thio-substituted coumarin, wherein the corrosion inhibition composition inhibits corrosion of a metal.

The present invention provides a method of inhibiting corrosion. The method includes contacting a metal with the heteroaryl-thio-substituted pyrone compound that is a heteroaryl-thio-substituted pyrone or a heteroaryl-thio-substituted coumarin, and/or contacting the metal with a reaction product thereof.

The present invention provides a metal having a decreased rate of corrosion. The metal includes a coating and/or adsorbed layer on an exterior surface of the metal including the heteroaryl-thio-substituted pyrone compound that is a heteroaryl-thio-substituted pyrone or a heteroaryl-thio-substituted coumarin.

The present invention provides a metal having a decreased rate of corrosion. The metal includes a coating and/or adsorbed layer on an exterior surface of the metal including a reaction product of: the heteroaryl-thio-substituted pyrone compound that is a heteroaryl-thio-substituted pyrone or a heteroaryl-thio-substituted coumarin; and (a) an acidic solution, or (b) the exterior surface of the metal, or (c) a combination thereof.

The present invention provides a method of forming the heteroaryl-thio-substituted pyrone compound that is a heteroaryl-thio-substituted pyrone or a heteroaryl-thio-substituted coumarin. The method includes reacting bromine-substituted pyrone or coumarin with a heteroaryl-thiol to form the heteroaryl-thio-substituted pyrone or heteroaryl-thio-substituted coumarin of claim 1.

In various embodiments, the heteroaryl-thio-substituted pyrone compounds of the present invention and methods of making and using the same can have advantages over other organic compounds, such as over other organic corrosion inhibitors. For example, in various embodiments, one or more starting materials of the heteroaryl-thio-substituted pyrone compounds of the present invention can be naturally (e.g., sustainably) sourced. In various embodiments, the heteroaryl-thio-substituted pyrone compounds of the present invention can have similar or greater corrosion inhibition activity for various metals as compared to other organic corrosion inhibitors. In various embodiments, the heteroaryl-thio-substituted pyrone compounds of the present invention can be more polarizable than other organic corrosion inhibitors. In various embodiments, the heteroaryl-thio-substituted pyrone compounds of the present invention can be inhibitors of biological nitrification. In various embodiments, the heteroaryl-thio-substituted pyrone compounds of the present invention provide wear inhibition to various metals (e.g., can be anti-wear compounds), having similar or greater anti-wear inhibition as compared to other organic anti-wear compounds.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
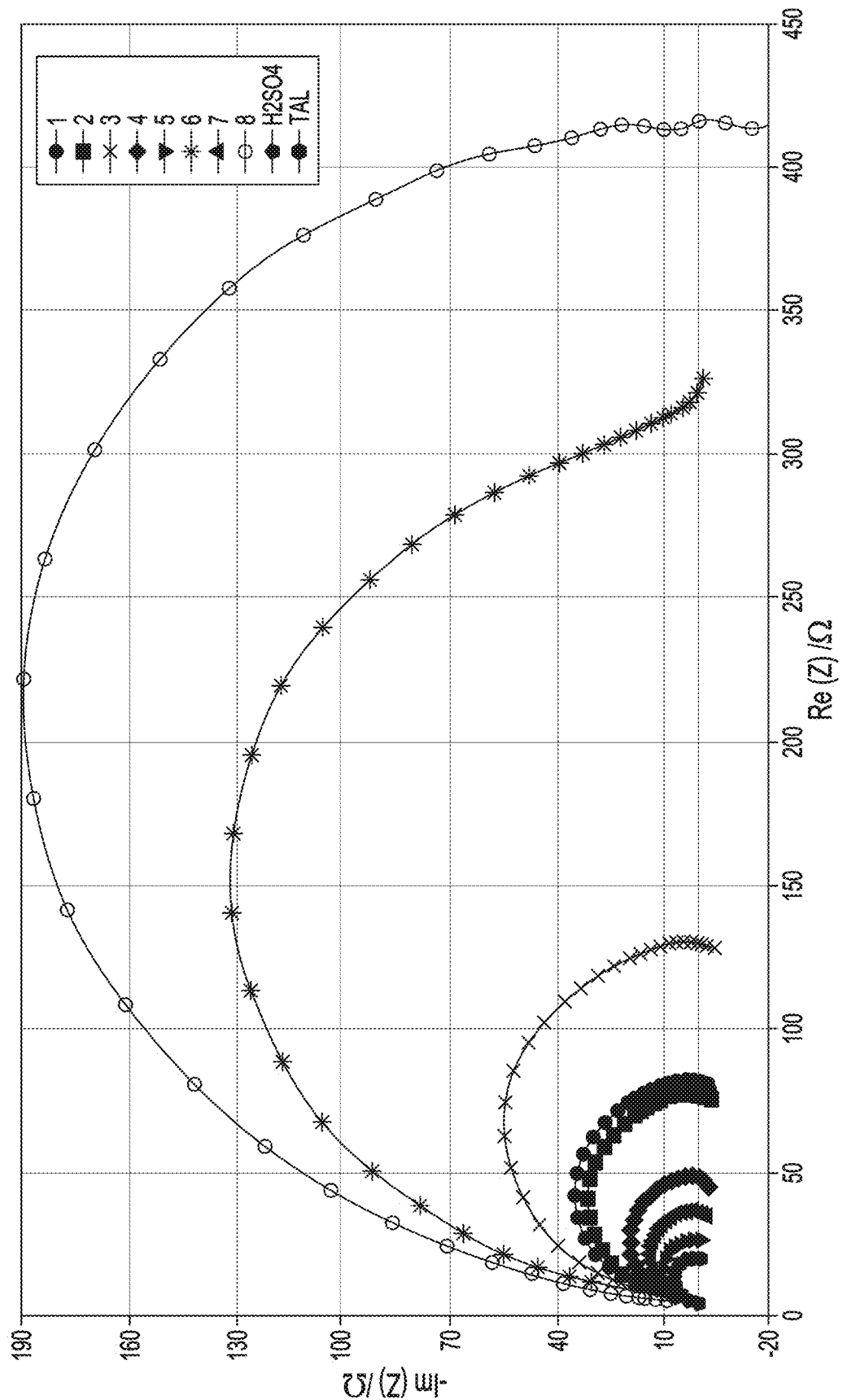
FIG. 1 illustrates a Nyquist plot of 1 mM concentration of various corrosion inhibitors and TAL in 0.1 M sulfuric acid at 30° C.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms, and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl). N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo [b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl. (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups. The term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a\text{-}C_b)$hydrocarbyl, wherein a and b are integers and mean having any of a to b number of carbon atoms. For example, $(C_1\text{-}C_4)$ hydrocarbyl means the hydrocarbyl group can be methyl $(C_1)$, ethyl $(C_2)$, propyl $(C_3)$, or butyl $(C_4)$, and $(C_0\text{-}C_b)$ hydrocarbyl means in certain embodiments there is no hydrocarbyl group. A hydrocarbylene group is a diradical hydrocarbon, e.g., a hydrocarbon that is bonded at two locations.

Heteroaryl-Thio-Substituted Pyrone Compound.

In various embodiments, the present invention provides a heteroaryl-thio-substituted pyrone compound. The heteroaryl-thio-substituted pyrone compound can be a heteroaryl-thio-substituted pyrone or a heteroaryl-thio-substituted coumarin. As used herein, pyrone refers to 2-pyrone. Coumarin can be considered a pyrone having a phenyl ring fused thereto at the 5-6 bond of the pyrone; therefore, as used herein, a coumarin is a species of substituted pyrone.

The heteroaryl-thio-substituted pyrone or heteroaryl-thio-substituted coumarin can be unsubstituted (other than the heteroaryl-thio-substituent), or can be further substituted. The pyrone or coumarin can be substituted with one or more of the heteroaryl-thio groups. The pyrone or coumarin can be substituted with a single one of the heteroaryl-thio groups. The substitution of the heteroaryl-thio group on the pyrone or coumarin can occur at any suitable location of the pyrone or coumarin. The pyrone or coumarin can be substituted at the 4-position with the heteroaryl-thio group.

The compound can be a heteroaryl-thio-substituted pyrone. The pyrone can be 6-methyl substituted and can be otherwise unsubstituted other than the heteroaryl-thio substitution. The compound can be a 4-heteroaryl-thio-substituted pyrone. The compound can be a 4-heteroaryl-thio-substituted 6-methylpyrone.

The compound can be a heteroaryl-thio-substituted coumarin. The coumarin can be unsubstituted other than the heteroaryl substitution. The compound can be a 4-heteroaryl-thio-substituted coumarin.

The compound can be in any suitable state of purity. The compound can be a part of a composition such that the concentration of the compound is any suitable concentration, such as 0.00001 wt % to 100 wt %, or 0.00001 wt % or less, or equal to or greater than 0.00001 wt %, 0.0001, 0.001, 0.01, 0.1, 0.5, 1, 1.5, 2, 3, 4, 5, 6, 8, 10, 15, 20, 25, 30, 35, 40, 45, 50, 55, 60, 65, 70, 75, 80, 85, 90, 95, 96, 97, 98, 99, 99.5, 99.9, 99.99, or 99.999 wt % or more. The compound can be at least 90 wt % pure, or at least 99 wt % pure (e.g., the compound can be part of a composition having a concentration of the compound of at least 90 wt %, or at least 99 wt %).

The heteroaryl-thio substituent can be derived from a thiol compound, wherein the thiol hydrogen is replaced by a bond to the pyrone or coumarin in the heteroaryl-thio-substituted pyrone or coumarin. The heteroaryl group can include heteroatoms such as nitrogen, sulfur, or a combination thereof, and can include a substituted or unsubstituted five- or six-membered heteroaryl ring. The heteroaryl-thio substituent can be derived from any suitable thiol compound, such as a cyclic or noncyclic thioamide or a cyclic or noncyclic thiourea. The heteraryl-thio substituent can be derived from a thiol chosen from:

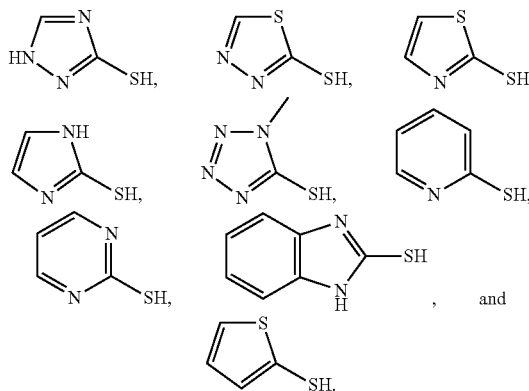

The heteroaryl-thio-substituted compound can be a heteroaryl-thio-substituted pyrone having a structure chosen from:

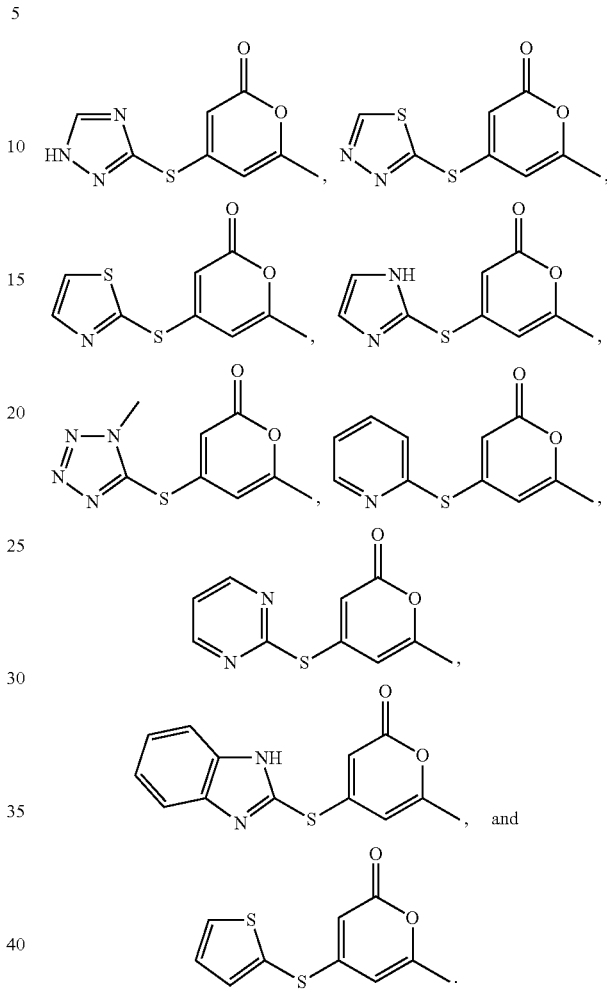

The heteroaryl-thio-substituted compound can be a heteroaryl-thio-substituted coumarin having a structure chosen from:

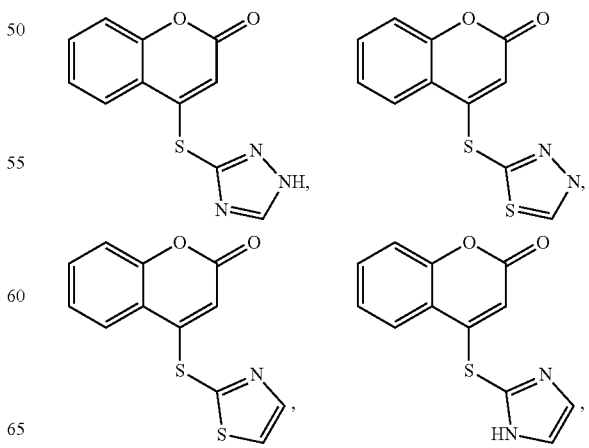

-continued

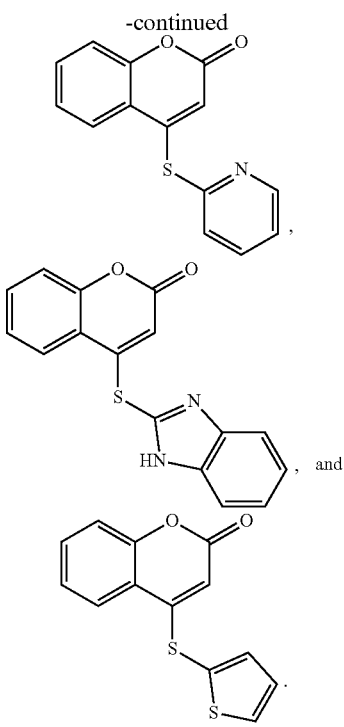

The heteroaryl-thio-substituted pyrone compound, or reaction products thereof, can have any suitable properties. In some embodiments, the compound is a corrosion inhibitor. In some embodiments, a reaction product of the compound, an acid, and a metal is a corrosion inhibitor of the metal.

The heteroaryl-thio-substituted pyrone compound can provide corrosion inhibition to a metal under any suitable conditions. In some embodiments, the compound can provide corrosion inhibition of the metal when in contact with the metal. In some embodiments, the compound can provide corrosion inhibition of metal with in contact with the metal under acidic conditions. A metal contacted with the compound under acidic conditions can exhibit inhibited corrosion. The metal removed from the acidic conditions under which the compound was contacted with the metal can continue to exhibit inhibited corrosion. The mechanism of corrosion inhibition of the metal can be any suitable mechanism, such as via reaction of the compound with the metal in the presence of an acid, and/or via adsorption of the compound on the metal in the presence of an acid.

In various embodiments, the heteroaryl-thio-substituted pyrone compound can provide inhibition of biological nitrification. In various embodiments, the compound can provide anti-wear properties to a metal.

The metal to which the compound or a reaction product thereof provides corrosion inhibition can be any suitable metal that can experience corrosion in the absence of the compound or reaction product thereof. For example, the metal can be a metal that includes iron or an alloy thereof. The metal can be a metal that includes aluminum, copper, iron, zinc, an alloy thereof, or a combination thereof. The metal can be or include steel. The metal can be or include a carbon steel, an alloy steel, or a combination thereof. The metal can include iron and also include manganese, nickel, chromium, molybdenum, boron, titanium, vanadium, tungsten, cobalt, niobium, or a combination thereof.

Composition Including the Heteroaryl-Thio-Substituted Pyrone Compound.

In various embodiments, the present invention provides a composition including the heteroaryl-thio-substituted pyrone compound that is a heteroaryl-thio-substituted pyrone or a heteroaryl-thio-substituted coumarin. The composition can be any suitable composition that includes the compound. The composition can be a corrosion inhibition composition that inhibits corrosion of a metal via treatment thereof with the composition. The composition can be a paint, a coating, a spray, a lubricant composition (e.g., that provides increased lubrication to a material such as a metal treated therewith), a metal wear-protection composition (e.g., that provides wear inhibition of metal treated therewith), a soil-treatment composition (e.g., that provides inhibition of biological nitrification), or a combination thereof.

The composition including the heteroaryl-thio-substituted compound can have any suitable concentration of the heteroaryl-thio-substituted compound, such as 0.00001 wt % to 100 wt %, or 0.00001 wt % or less, or equal to or greater than 0.00001 wt %, 0.0001, 0.001, 0.01, 0.1, 0.5, 1, 1.5, 2, 3, 4, 5, 6, 8, 10, 15, 20, 25, 30, 35, 40, 45, 50, 55, 60, 65, 70, 75, 80, 85, 90, 95, 96, 97, 98, 99, 99.5, 99.9, 99.99, or 99.999 wt % or more.

The composition including the heteroaryl-thio-substituted compound can include any suitable additional components. For example, the composition can include water, an organic solvent, acid, base, buffer, one or more additional corrosion inhibiting compositions, additives, or a combination thereof. The composition can be an aqueous composition including acid.

A corrosion inhibiting composition including the heteroaryl-thio-substituted composition that inhibits corrosion of a metal via treatment therewith can have any suitable mechanism of corrosion inhibition. For example, the composition can provide inhibited corrosion of the metal during contacting of the composition with the metal or during contacting of a reaction product of the compound and/or of the composition with the metal. The composition can provide inhibited corrosion of the metal after contacting the composition or a reaction product of the compound and/or of the composition with the metal (e.g., after removing the metal from a composition including the compound, which can leave a residual coating and/or adsorbed layer of the compound and/or reaction products thereof on the surface of the metal).

Method of Inhibiting Corrosion.

In various embodiments, the present invention provides a method of inhibiting corrosion. The method can include contacting a metal with the heteroaryl-thio-substituted pyrone compound, a reaction product thereof, or a combination thereof.

The method can include contacting the metal with the heteroaryl-thio-substituted pyrone compound or reaction product thereof under any suitable conditions, such as neutral, acidic, or basic conditions. The method can including contacting the metal with the compound or reaction product thereof under acidic conditions. For example, the method can include contacting the metal with an aqueous acidic solution that includes the compound and/or a reaction product thereof. The method can further include removing the metal from a solution including the compound, which can leave a residual coating and/or adsorbed layer of the compound and/or a reaction product thereof on the surface of the metal that has a corrosion inhibiting effect. The method can include rinsing the metal after removal from a solution including the compound and/or reaction product thereof, such as to remove residual solution from the surface of the metal while leaving a residual coating and/or adsorbed layer of the compound and/or reaction product thereof on the surface of the metal.

The corrosion inhibiting effect can occur via any suitable mechanism. The corrosion inhibiting effect can be caused by the compound itself, a reaction product of the compound and the metal surface, a reaction product of the compound and acid, a reaction product of the compound and acid and the metal, or a combination thereof. The corrosion inhibiting effect can be provided during acidic conditions used to expose the compound and/or reaction product thereof to the surface of the metal. The corrosion inhibiting effect can be provided after exposure to acidic conditions used to expose the compound and/or reaction product thereof to the surface of the metal.

The metal can be any suitable metal that can experience corrosion in the absence of the compound or reaction product thereof. For example, the metal can be a metal that includes iron or an alloy thereof. The metal can be or include steel. The metal can be or include a carbon steel, an alloy steel, or a combination thereof. The metal can include iron and also include manganese, nickel, chromium, molybdenum, boron, titanium, vanadium, tungsten, cobalt, niobium, or a combination thereof.

Metal Having a Decreased Rate of Corrosion.

Various embodiments provide a metal having a decreased rate of corrosion. The metal can include a coating on an exterior surface of the metal. The coating can include the heteroaryl-thio-substituted pyrone compound, a reaction product thereof, or a combination thereof. The coating can include or be an adsorbed layer of the heteroaryl-thio-substituted pyrone compound, a reaction product thereof, or a combination thereof. The reaction product can be a reaction product of the heteroaryl-thio-substituted pyrone compound and any suitable one or more materials, such as (a) an acidic solution, or (b) the exterior surface of the metal, or (c) a combination thereof.

Method of Forming the Heteroaryl-Thio-Substituted Pyrone Compound.

In various embodiments, the present invention provides a method of forming the heteroaryl-thio-substituted pyrone compound. The method can be any suitable method that forms the heteroaryl-thio-substituted pyrone compound. For example, the method can include reacting a halogen-substituted (e.g., bromine-substituted) pyrone or coumarin with a heteroaryl-thiol to form the heteroaryl-thio-substituted pyrone or heteraryl-thio-substituted coumarin.

In various embodiments, a pyrone or coumarin starting material used to form the heteroaryl-thio-substituted pyrone or coumarin can be naturally (e.g., sustainably) derived. For example, a method of forming the heteroaryl-thio-substituted pyrone can use a triacetic acid lactone starting material. Triacetic acid lactone can be derived enzymatically from glucose, and can be a product of fermentation. In another example, a method of forming the heteroaryl-thio-substituted coumarin can use a 4-hydroxycoumarin starting material. 4-Hydroxycoumarin can be a fungal metabolite of coumarin, and as such it can be sustainably derived.

Examples

Various embodiments of the present invention can be better understood by reference to the following Examples which are offered by way of illustration. The present invention is not limited to the Examples given herein.

Synthesis of Organic Corrosion Inhibitors Based on TAL or 4-Hydroxycoumarin.

All starting materials were purchased from Sigma-Aldrich, AK Scientific Institution and Oakwood Chemical; Solvents were all purchased from Sigma-Aldrich and Fisher Scientific and used without further distillation. All reactions were monitored by thin layer chromatography (TLC) and $^1$H NMR. All yields refer to separated yield after column chromatography unless indicated. TLC was obtained by silica plate using UV light as a visualizing agent or potassium permanganate solution with heat. All columns were performed with silica gel 60 Å, particle size 40-63 m. $^1$H and $^{13}$C NMR spectra were acquired in CDCl$_3$ or other deuterated solvents on a Varian MR-400 or Bruker Avance III 600 MHz spectrometer. All mass spectrums were obtained on an Agilent 6540 QTOF spectrometer.

Development of the various corrosion inhibitors utilized triacetic acid lactone and PBr$_3$ to substitute the hydroxyl group for the bromine (Scheme 1). The first step was performed in a round bottom flask, a solution of PBr$_3$ (45 mmol, 1.5 equiv., 8.43 mL) in diethyl ether (22 mL) is added to DMF (100 mL, [0.33M]) at 0° C. and stirred for 1 hour. Then, triacetic acid lactone (30 mmol, 1 equiv., 3.78 g) is added to the solution, and the solution heated to 60° C. overnight. The reaction is monitored by TLC, and once the starting material is consumed, 200 mL H$_2$O is added and the mixture extracted with diethyl ether (3×50 mL). The solvent is evaporated under reduced pressure and then filtered. The filter cake is washed with DCM, and the filtrate is evaporated under reduced pressure, and the residue is subjected to silica gel column chromatography. The yield of 4-bromotriacetic acid lactone is 81%.

Scheme 1. Synthesis of corrosion inhibitors based on triacetic acid lactone (TAL).

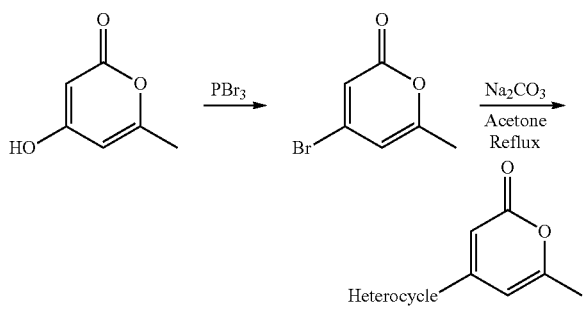

The second step produced products of 1-8 in good yields by introducing a nucleophilic heterocycle. 1 mmol of 4-bromotriacetic acid lactone was added to a round bottom flask with 5 mmol Na$_2$CO$_3$, 5 mL of acetone, and 1.1 mmol of a corresponding heterocycle. The mixture was stirred at room temperature overnight. The reaction was monitored by TLC and was filtered to remove Na$_2$CO$_3$, and washed with acetone. Solvent was then removed with reduced pressure and a yellow solid formed. The solid would be passed through silica column with ethyl acetate mobile phase. Further purification was performed by trituration with n-hexanes.

The synthesis of corrosion inhibitors based on 4-hydroxycoumarin was shown in Scheme 2 following a procedure developed by Balalas, T.; Abdul-Sada, A.; Hadjipavlou-Litina. D. J.; Litinas, K. E., Pd-Catalyzed Efficient Synthesis of Azacoumestans Via Intramolecular Cross Coupling of 4-(Arylamino)coumarins in the Presence of Copper Acetate under Microwaves. Synthesis-Stuttgart 2017, 49 (11), 2575-2583. The first step was performed in a round bottom flask, where 4-hydroxycoumarin (30.8 mmol, 1 equiv., 5.00 g) in toluene (62 mL. [0.5M]) was heated under argon at 100° C. Tetrabutylammoniumbromide (46.3 mmol, 1.5 equiv., 14.91 g) was then added and the mixture was heated to become a solution. Phosphorus pentoxide (61.7 mmol, 2 equiv., 8.75 g) was added and the mixture was heated for 3 h. The hot upper organic layer was transferred to a separatory funnel and the lower later was extracted with boiling toluene (2×30 mL). The combined toluene layers were washed with 5% aq. NaHCO$_3$ (2×30 mL), H$_2$O (30 mL), and satd. aq. NaCl (30 mL). This was dried over sodium sulfate and concentrated under reduced pressure. The yield of 4-bromocoumarin was 74%.

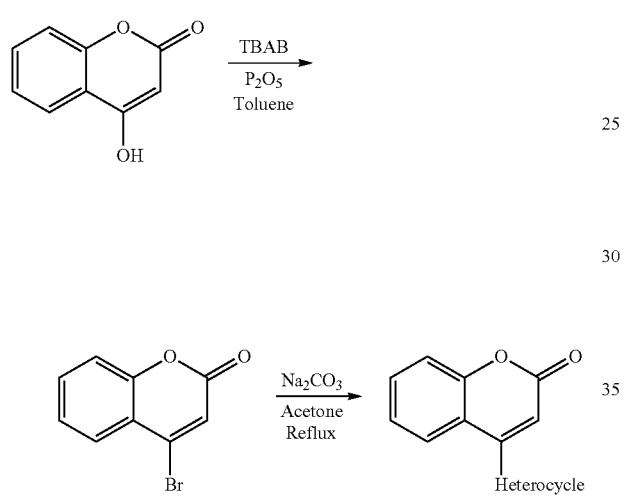

Scheme 2. Synthesis of corrosion inhibitors based on 4-hydroxycoumarin (4HC).

In second step, a solution of the corresponding heterocycle (3.3 mmol, 1.1 equiv.) in acetone ([0.2 M]) was added Na$_2$CO$_3$ (15 mmol, 5 equiv., 1.5898 g) and 4-bromocoumarin (3 mmol, 1 equiv., 0.6751 g) sequentially. This reaction was monitored by TLC and filtered to remove Na$_2$CO$_3$. The filter cake was washed with acetone. Solvent was removed under reduced pressure and the residue was chromatographed on silica gel.

$^1$H NMR and MS Identification of the Synthesized Molecules.

Product 1 had the following $^1$H NMR and MS data: $^1$H NMR (400 MHz, DMSO-d$_6$) δ 8.80 (s, 1H), 6.19 (s, 1H), 5.74 (d, J=1.7 Hz, 1H), 2.17 (s, 3H). MS 209 M/Z.

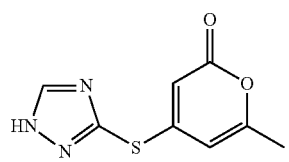

Product 2 had the following $^1$H NMR and MS data: $^1$H NMR (400 MHz, DMSO-d$_6$) δ 9.90 (s, 1H), 6.32-6.26 (m, 1H), 5.93 (t, J=1.2 Hz, 1H), 2.19 (s, 3H). MS 225 M/Z.

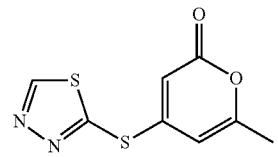

Product 3 had the following $^1$H NMR and MS data: $^1$H NMR (400 MHz, DMSO-d$_6$) δ 8.19-8.11 (m, 2H), 6.22 (dd, J=1.8, 1.0 Hz, 1H), 5.69-5.64 (m, 1H), 2.19-2.17 (m, 3H). MS 224 M/Z.

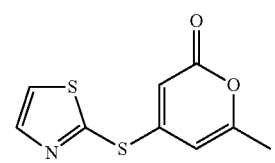

Product 4 had the following $^1$H NMR and MS data: $^1$H NMR (400 MHz, DMSO-d$_6$) δ 7.23 (s, 2H), 6.05 (dd, J=1.9, 1.0 Hz, 1H), 5.37 (dd, J=1.7, 0.7 Hz, 1H), 2.15 (s, 3H). MS 208 M/Z.

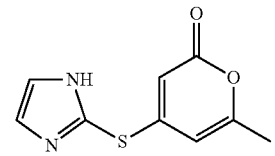

Product 5 had the following $^1$H NMR and MS data: $^1$H NMR (400 MHz, DMSO-d$_6$) δ 6.23-6.20 (m, 1H), 5.86-5.82 (m, 1H), 4.07 (d, J=1.1 Hz, 3H), 2.20-2.16 (m, 3H). MS 224 M/Z.

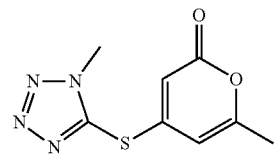

Product 6 had the following ¹H NMR and MS data: ¹H NMR (400 MHz, CDCl₃) δ 8.66 (ddd, 1H, J=4.8, 1.9, 0.9 Hz), 7.75 (td, 1H, J=7.6, 1.9 Hz), 7.54 (dt, 1H, J=7.8, 0.9 Hz), 7.33 (ddd, 1H, J=7.6, 4.9, 1.1 Hz), 5.91 (dd, 1H, J=1.7, 0.9 Hz), 5.86 (dd, 1H, J=1.7, 0.6 Hz), 2.19 (s, 3H). M/Z 219.

The following product had the following ¹H NMR and MS data: ¹H NMR (400 MHz, DMSO-d₆) δ 8.23 (dd, J=8.9, 3.4 Hz, 2H), 7.88 (dd, J=7.6, 1.4 Hz, 1H), 7.74 (ddd, J=8.5, 7.0, 2.7 Hz, 1H), 7.50-7.43 (m, 2H), 5.84 (s, 1H). M/Z 261.

6

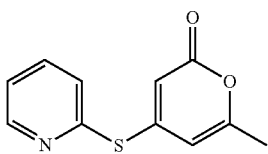

Product 7 had the following ¹H NMR and MS data: ¹H NMR (400 MHz, DMSO-d₆) δ 8.79 (d, J=4.9 Hz, 2H), 7.45 (t, J=4.9 Hz, 1H), 6.72 (d, J=1.5 Hz, 1H), 6.43 (s, 1H), 2.21 (s, 3H). MS 220 M/Z.

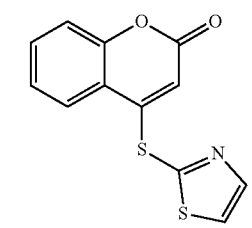

7

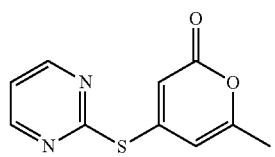

Product 8 had the following ¹H NMR and MS data: ¹H NMR (400 MHz, DMSO-d₆) δ 7.52 (dd, J=6.2, 3.3 Hz, 2H), 7.09 (dd, J=6.2, 3.3 Hz, 2H), 6.22 (s, 1H), 6.03 (s, 1H), 2.17 (s, 3H). MS 258 M/Z

8

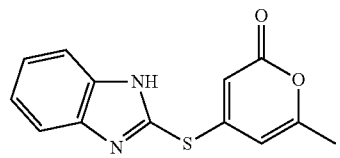

The following product had the following ¹H NMR and MS data: ¹H NMR (400 MHz, DMSO-d₆) δ 8.92 (s, 1H), 7.88 (dd, J=7.6, 1.4 Hz, 1H), 7.73 (ddd, J=8.5, 7.0, 2.7 Hz 1H), 7.50-7.43 (m, 2H), 5.94 (s, 1H). M/Z 245.

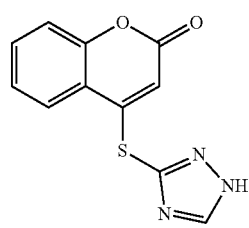 [SMILES: O=c1cc(Sc2nc[nH]n2)c2ccccc2o1]

Electrochemical Impedance Spectroscopy (EIS) Measurement.

A VSP-300 Potentiostat from Bio-logic with an EC-LAB software was used for EIS measurement. The test was performed in a conventional 3-electrode cell with an Ag/AgCl reference electrode, a Pt foil counter electrode and a mild steel coupon as working electrode. The counter electrode and working electrode were clamped using a PTFE holder sited in a PTFE cell head. A freshly made 1 mM of inhibitor in either 0.1 M sulfuric acid or 0.3M HCl solution was prepared and sonicated before each test. Mild steel A366/1008 (from Onlinemetals.com) was cut into 1 cm*3 cm coupon. The steel was manually polished with 600, 800, 1200, and 2000 grade sanding papers, then rinsed with ethanol and sonicated for 3 minutes. After being wiped with a Kimwipe, the steel coupon was wrapped in the center by parafilm to ensure that exposed end surface area was 1 cm² on each side. An aliquot of 40 mL of the acid solution was put in the cell, which was then put in a 30° C. water bath on a heating plate. An open circuit voltage was recorded and stabilized for 30 min. Electrochemical impedance measurements were performed at the open circuit voltage. Frequency ranged from $10^5$ to $10^{-1}$ Hz with an amplitude of 10 mV was used for the test. After the analysis, the built-in software was used to do the Z-fit of Randles equivalent circuit with a constant phase element to obtain charge transfer resistance. Based on the charge transfer resistance, the inhibition efficiency was calculated.

Results and Discussion.

The synthesized corrosion inhibitors included the eight different triacetic acid lactone (TAL)-based corrosion inhibitors (1-8) shown in Scheme 3, which were synthesized in good yield. The yields are all above 80% except for 5. Scheme 4 shows heterocycles 1.5-8.5 used for the synthesis of inhibitors 1-8.

Scheme 3. Organic corrosion inhibitors (1-8) based on triacetic acid lactone (TAL) and synthesis yield. The yield was calculated on the 4-bromotriacetic acid lactone.

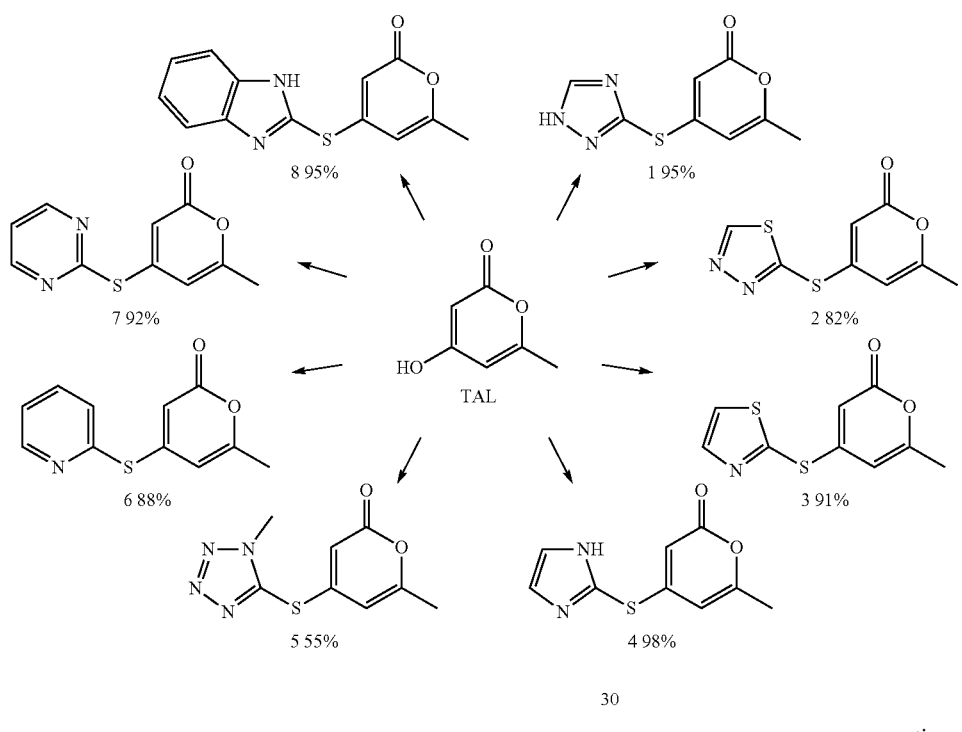

Scheme 4. Heterocycles (1.5-8.5) used in the synthesis for organic corrosion inhibitors (1-8) in Scheme 3.

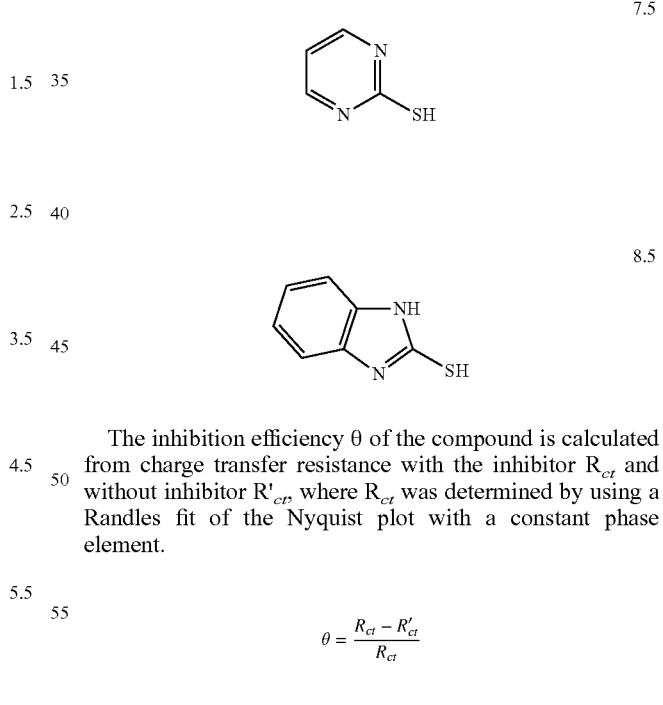

The inhibition efficiency θ of the compound is calculated from charge transfer resistance with the inhibitor $R_{ct}$ and without inhibitor $R'_{ct}$, where $R_{ct}$ was determined by using a Randles fit of the Nyquist plot with a constant phase element.

$$\theta = \frac{R_{ct} - R'_{ct}}{R_{ct}}$$

Hexamthylenetetramine (HTMA) has been identified as an effective organic corrosion inhibitor in many research studies and was used as reference material in our study. As can be seen in Table 1 and FIG. 1, the synthesized molecules besides 5 showed a better corrosion inhibition efficiency than HTMA in 0.1 M sulfuric acid. FIG. 1 illustrates a Nyquist plot of 1 mM concentration of various corrosion inhibitors and TAL in 0.1 M sulfuric acid at 30° C. Detailed analysis of the starting materials showed that TAL is not a corrosion inhibitor at all with 0% of inhibition efficiency. Inhibition efficiency was usually improved when attached the heterocycle to the TAL compound except for 4 and 7, where IE decreased when the heterocycle was attached to TAL. 1, 2, 3, 6, 8 all showed good IE values. 8 showed the best IE value which is possibly due to the starting molecule 8.5. Hexamethylenetetramine (i.e., HTMA or urotropin) had a Ret/Ohm of 23 and an IE of 30%.

Figure 2:
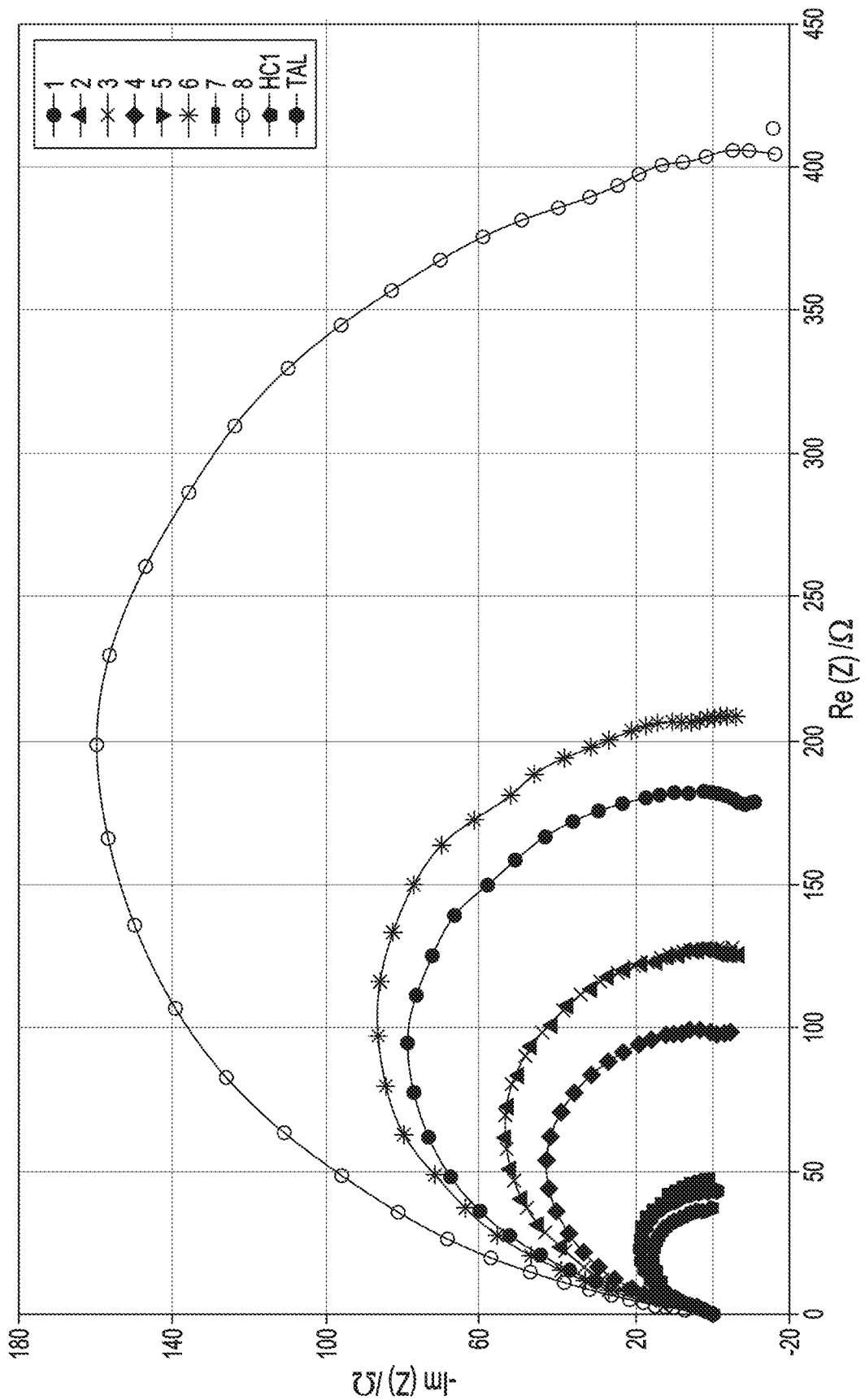
FIG. 2 illustrates a Nyquist plot of 1 mM concentration of the corrosion inhibitors (1-8) and TAL in 0.3M hydrochloric acid at 30° C.

A similar result was obtained from EIS testing in 0.3 M HCl solution, as shown in Table 2 and FIG. 2. FIG. 2 shows a Nyquist plot of 1 mM concentration of the various corrosion inhibitors and TAL in 0.3 M hydrochloric acid at 30° C. The inhibitors 1, 2, 3, 6, 8 all showed good IE values with 8 showed the best IE value. HTMA had a Rct/Ohm of 87 and an IE of 59%.

TABLE 1

Corrosion inhibition efficiency (IE) of the synthesized triacetic acid lactone-based corrosion inhibitors, and also separately of the starting materials, in 0.1M sulfuric acid at 30° C. from EIS testing.

| Label | $H_2SO_4$ | | | |
|---|---|---|---|---|
| Rct/Ohm | 16 | 77 | 73 | 126 |
| IE | NA | 79% | 78% | 87% |
| Label | TAL | | | |
| Rct/Ohm | 16 | 18 | 19 | 99 |
| IE | 0% | 11% | 16% | 84% |
| Label | $H_2SO_4$ | | | |
| Rct/Ohm | 16 | 44 | 22 | 306 |
| IE | NA | 64% | 27% | 95% |
| Label | TAL | | | |
| Rct/Ohm | 16 | 71 | 8 | 145 |
| IE | 0% | 77% | −100% | 89% |
| Label | $H_2SO_4$ | | | |
| Rct/Ohm | 16 | 32 | 415 | 229 |
| IE | NA | 50% | 96% | 93% |
| Label | TAL | | | |
| Rct/Ohm | 16 | 171 | 270 | NA |
| IE | 0% | 91% | 94% | |

TABLE 2

Corrosion inhibition efficiency (IE) of the synthesized corrosion inhibitors, and also separately of the starting molecules, in 0.3M hydrochloric acid at 30° C. from EIS testing.

| Label | HCl | Compound | Compound | Compound |
|---|---|---|---|---|
| Rct/Ohm | 36 | 179 | 125 | 125 |
| IE | NA | 80% | 71% | 71% |
| Label | TAL | | | |
| Rct/Ohm | 41 | 44 | 24 | 51 |
| IE | 12% | 18% | −50% | 29% |
| Label | HCl | | | |
| Rct/Ohm | 36 | 98 | 40 | 205 |
| IE | NA | 63% | 10% | 82% |
| Label | TAL | | | |
| Rct/Ohm | 41 | 68 | 11 | 142 |
| IE | 12% | 47% | −227% | 75% |
| Label | HCl | | | |
| Rct/Ohm | 36 | 43 | 389 | 141 |
| IE | NA | 16% | 91% | 74% |
| Label | TAL | | | |
| Rct/Ohm | 41 | 134 | 241 | |
| IE | 12% | 73% | 85% | |

Figure 3:
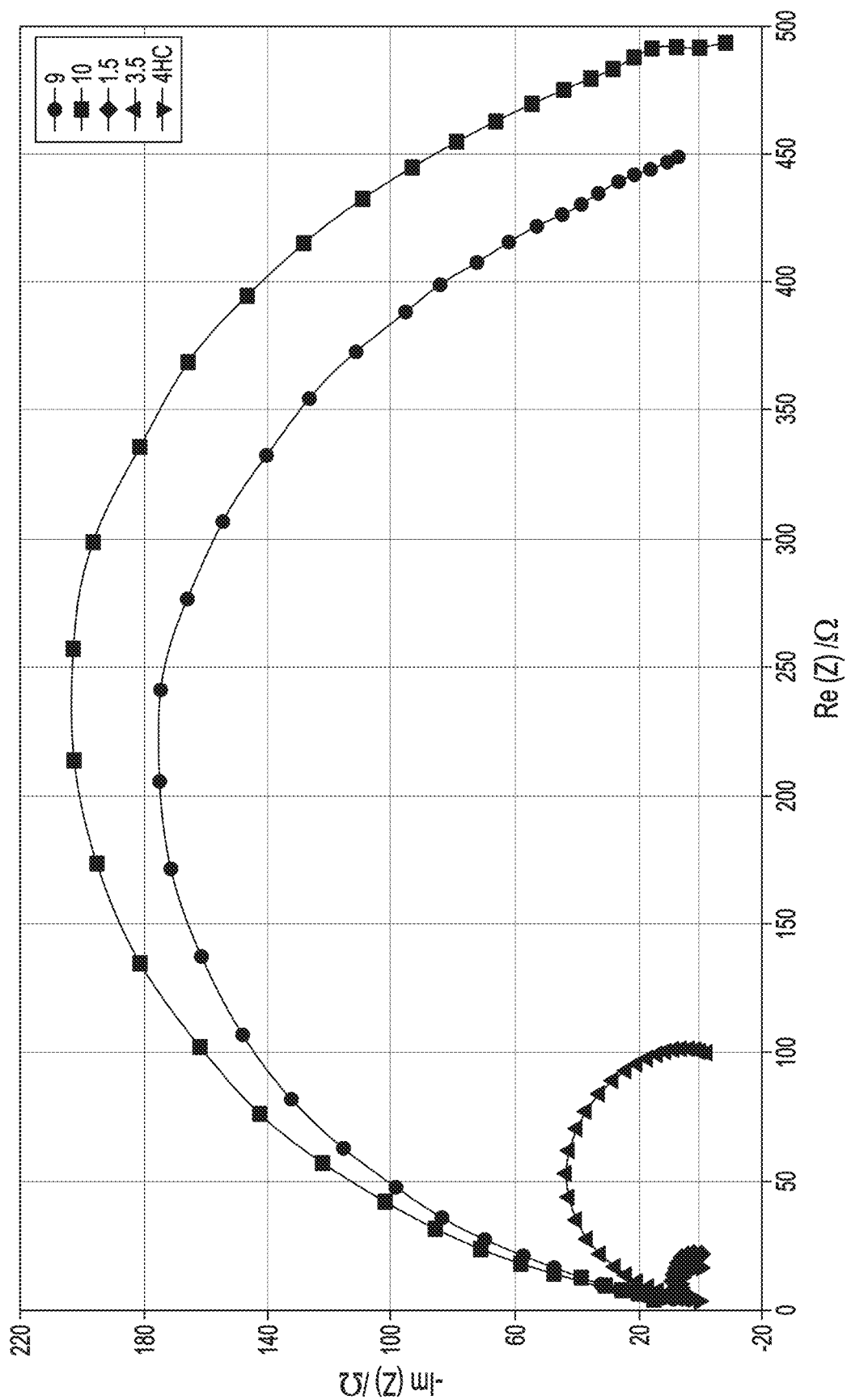
FIG. 3 shows a Nyquist plot of 1 mM concentration of the corrosion inhibitors (9-10), heterocycles 1.5 and 3.5, and 4HC in 0.1 M sulfuric acid at 30° C.
Figure 4:
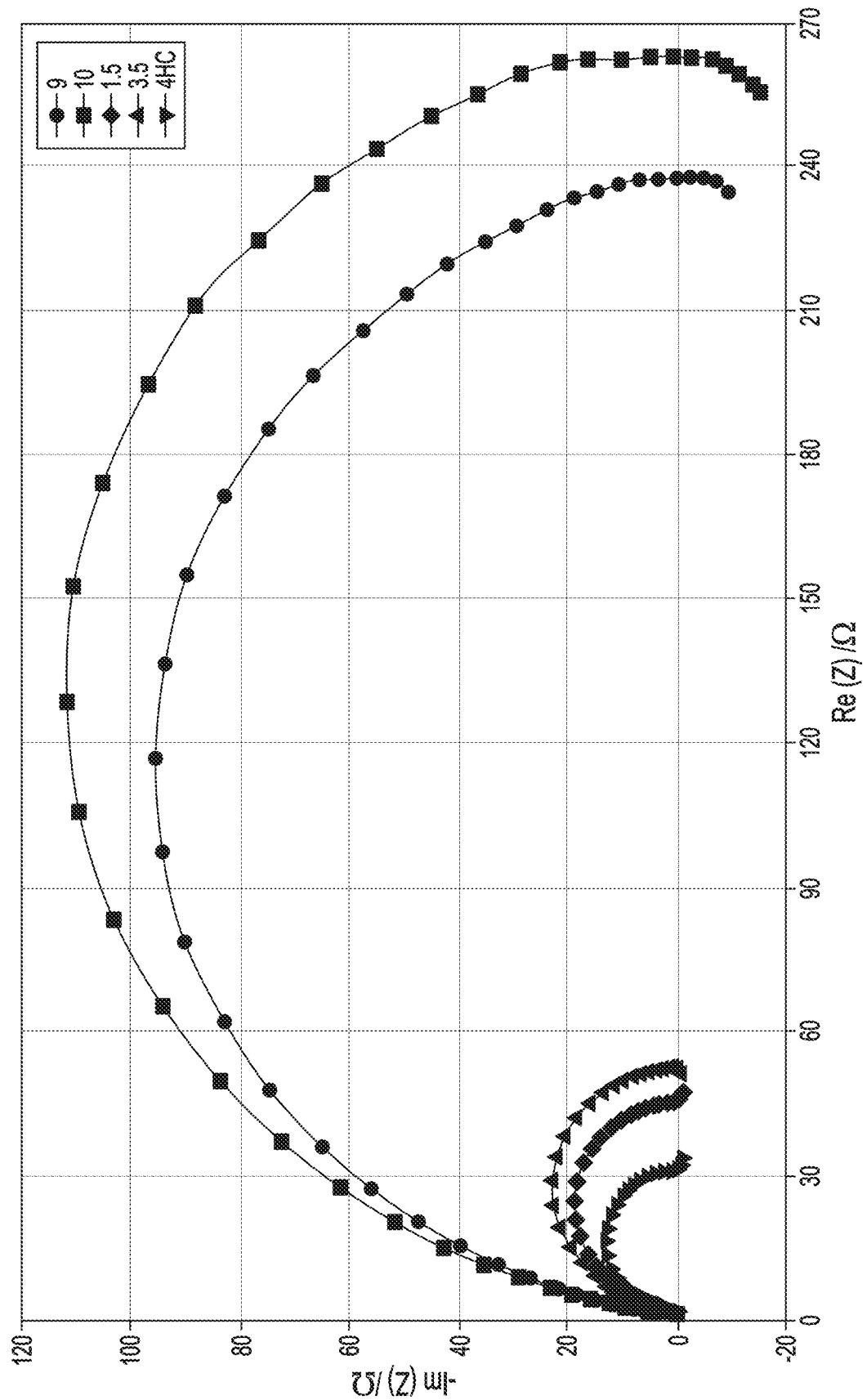
FIG. 4 shows a Nyquist plot of 1 mM concentration of the corrosion inhibitors (9-10), heterocycles 1.5 and 3.5, and 4HC in 0.3M hydrochloric acid at 30° C.

4-Hydroxycoumarin has a similar 2-pyrone structure with TAL but with an additional benzene ring. Scheme 5 illustrates the corrosion inhibitors formed based on 4-hydroxycoumarin. 4-Hydroxycoumarin is a fungal metabolite and can be synthesized by enzyme. 4-Hydroxycoumarin (4HC) alone is a corrosion accelerator instead of inhibitor in both hydrochloric acid and sulfuric acid, see Tables 3 and 4. Then we attached heterocycles to 4-hydroxycoumarin with good yields. 4-Hydroxycoumarin with Heterocycle 1.5 and 3.5 were chosen because synthesized molecule 1 and 3 showed improved performance and a good IE value in both hydrochloric acid and sulfuric acid solution. See Table 3 and FIG. 3, the synthesized molecules 9 and 10 based on 4-hydroxycoumarin (4HC) showed a better IE value than all the compounds based on TAL in sulfuric acid. FIG. 3 shows a Nyquist plot of 1 mM concentration of the corrosion inhibitors (9-10), heterocycles 1.5 and 3.5, and 4HC in 0.1 M sulfuric acid at 30° C. Further testing in hydrochloric acid solution showed good IE values in Table 4 and FIG. 4. FIG. 4 shows a Nyquist plot of 1 mM concentration of the corrosion inhibitors (9-10). heterocycles 1.5 and 3.5, and 4HC in 0.3 M hydrochloric acid at 30° C.

Figure 5:
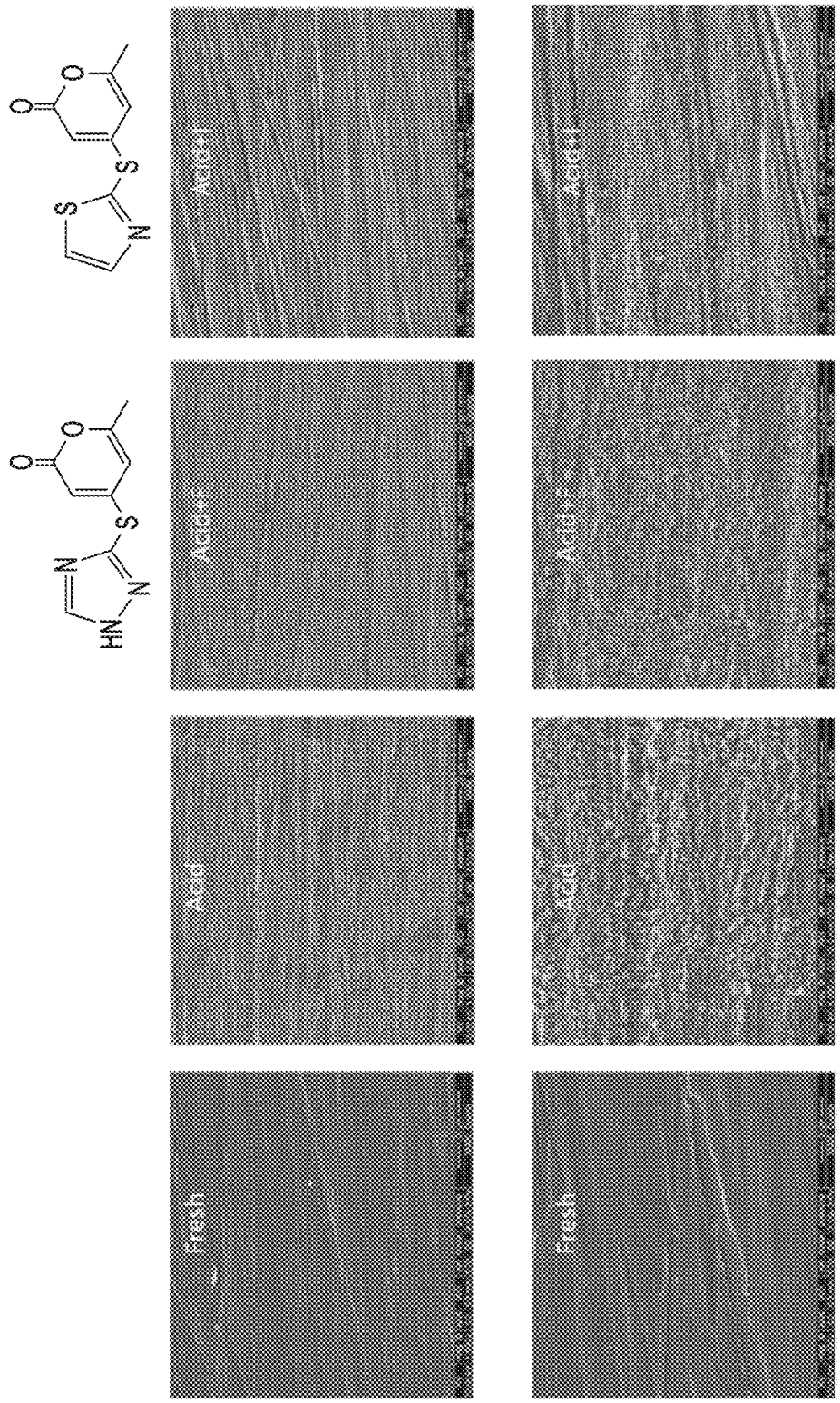
FIG. 5 shows SEM images of metal coupons that were fresh, after treatment with acid, or after treatment with acid in the presence of various synthesized corrosion inhibitors.
Figure 6A:
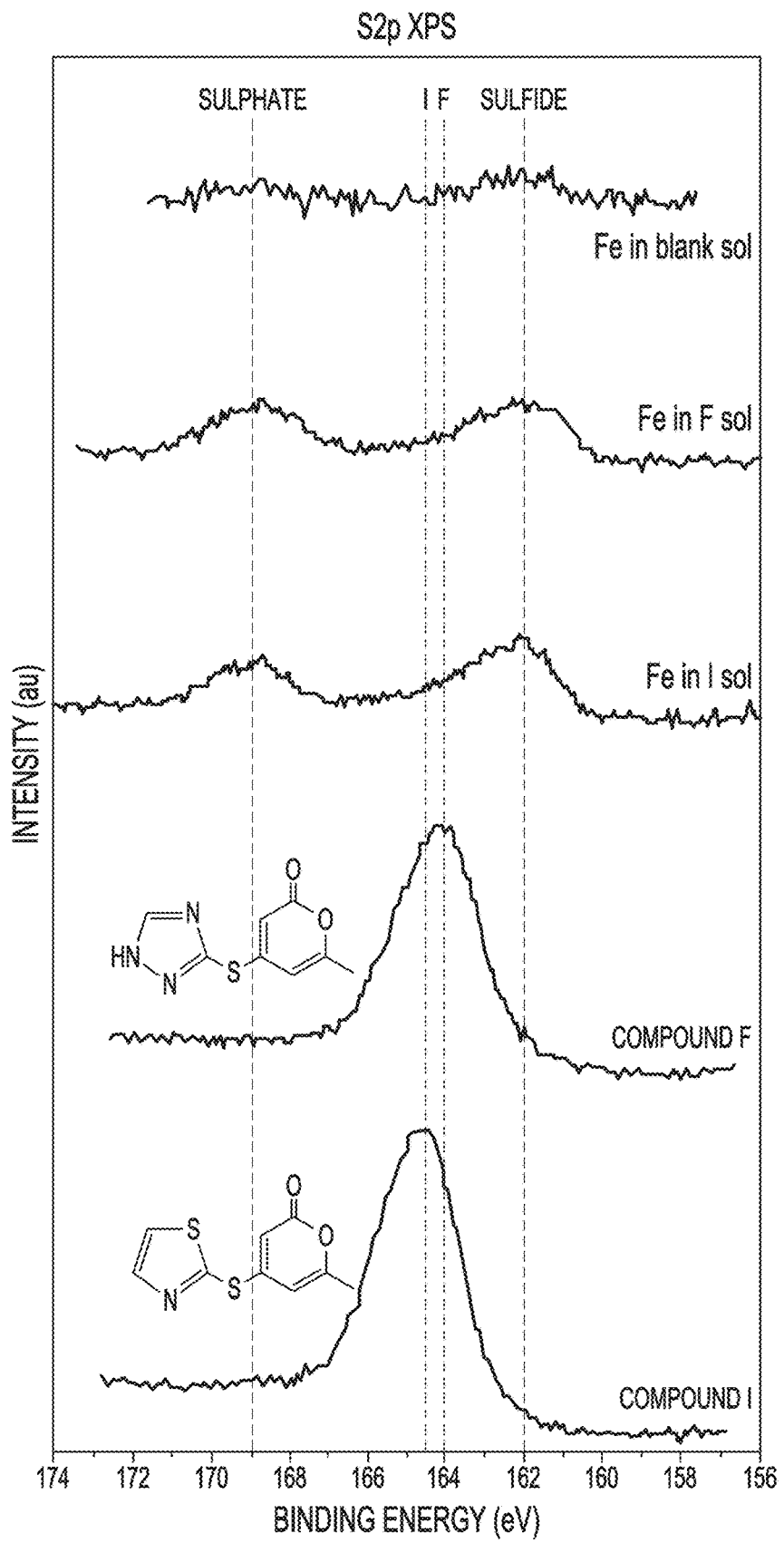
FIGS. 6a-b show XPS analyses of various synthesized corrosion inhibitors, and of metal coupons that were fresh or after treatment with the corrosion inhibitors in acid.
Figure 6B:
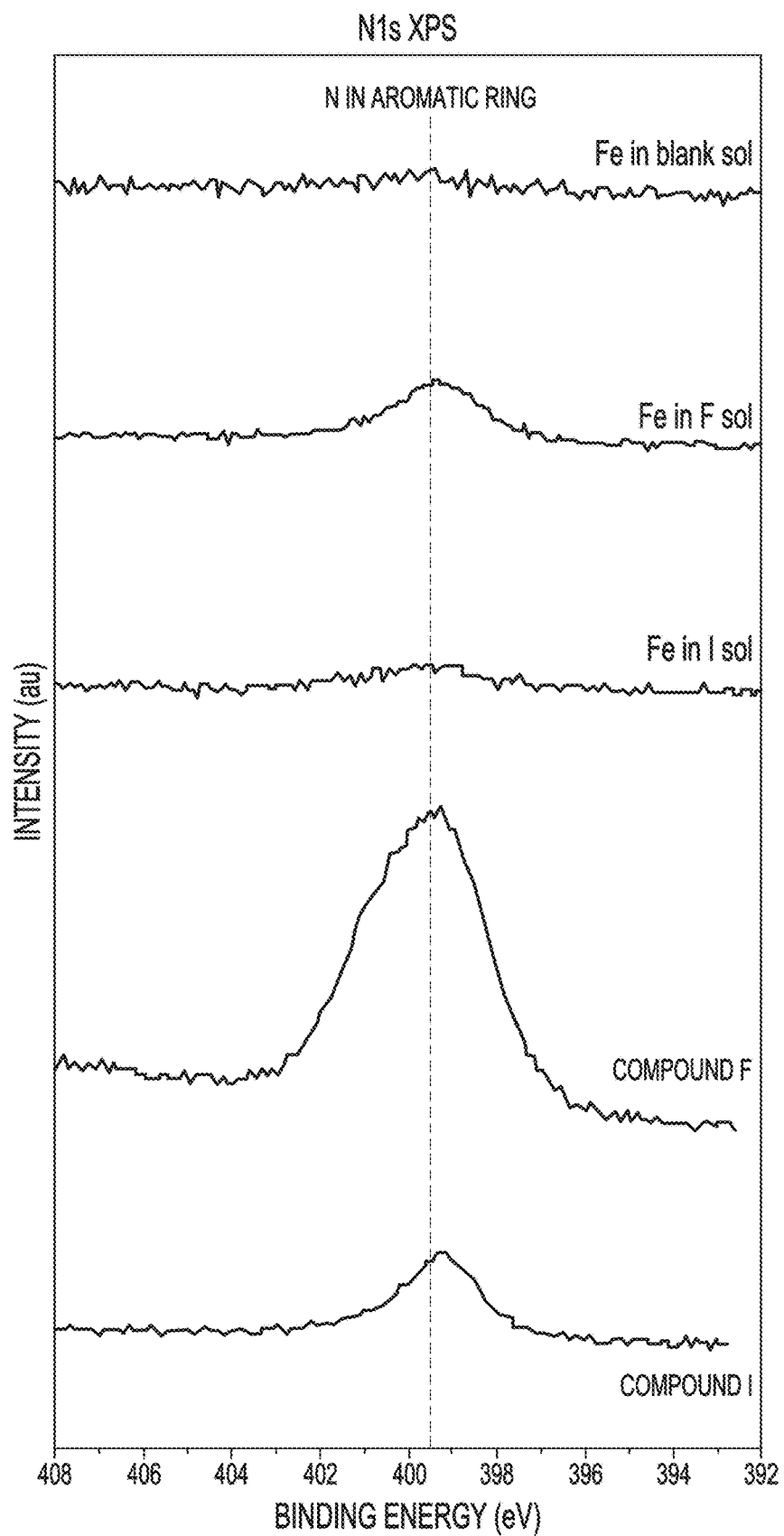

FIG. 5 shows SEM images of metal coupons that were fresh, after treatment with acid, or after treatment with acid in the presence of various synthesized corrosion inhibitors. FIGS. 6a-b show XPS analyses of various synthesized corrosion inhibitors, and of metal coupons that were fresh or after treatment with the corrosion inhibitors in acid. To prepare the metal coupon for SEM or XPS analysis, the mild steel coupon was treated in 40 mL of 0.1 M sulfuric acid solution including 1 mM inhibitor at 30° C. for 2 h. followed by water rinsing and drying.

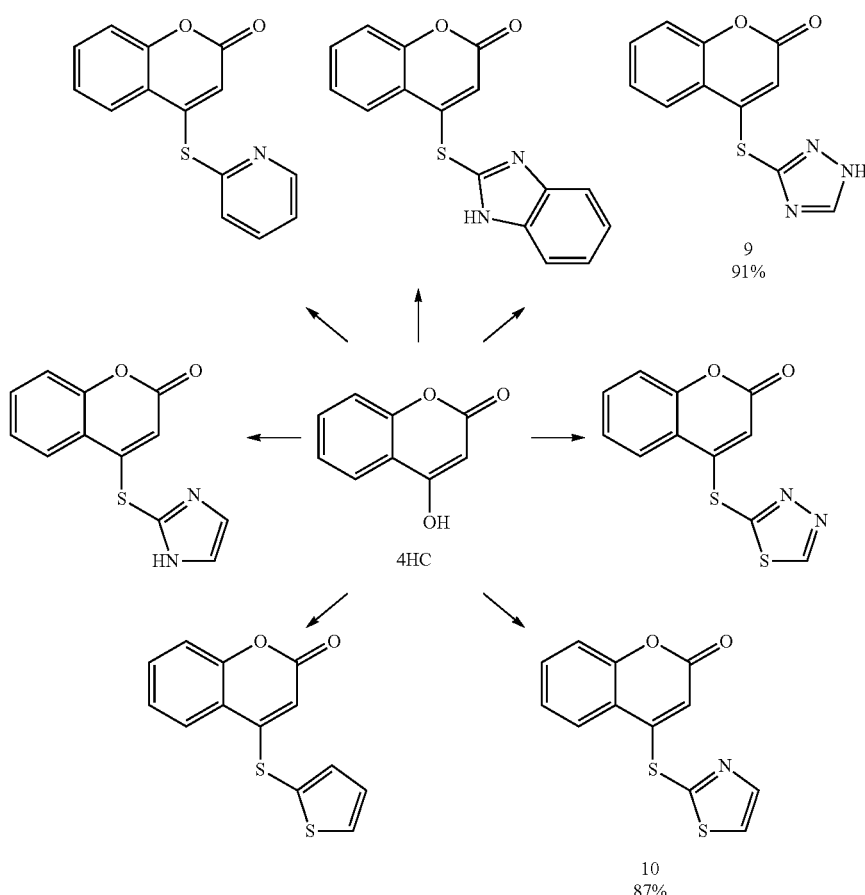

Scheme 5.
Organic corrosion inhibitors including compounds 9 and 10 based on 4-hydroxycoumarin (4HC) and synthesis yield. Yield was calculated based on 4-bromocoumarin.

TABLE 3

Corrosion inhibition efficiency (IE) of the synthesized corrosion inhibitor molecules based on 4-hydroxycoumarin, triacetic acid lactone-based corrosion inhibitors, and separately of the starting materials, in 0.1M sulfuric acid at 30° C. from EIS testing.

| Label | $H_2SO_4$ | | | | |
|---|---|---|---|---|---|
| Rct/Ohm | 16 | 478 | 397 | 430 | 269 |
| IE | NA | 97% | 96% | 96% | 94% |

TABLE 3-continued

Corrosion inhibition efficiency (IE) of the synthesized corrosion inhibitor molecules based on 4-hydroxycoumarin, triacetic acid lactone-based corrosion inhibitors, and separately of the starting niaterials, in 0.1M sulfuric acid at 30° C. from EIS testing.

| Label   | H₂SO₄ | [triazole-S-pyranone] | [thiadiazole-S-pyranone] | [thiazole-S-pyranone] | [imidazole-S-pyranone] |
|---------|-------|-----------------------|---------------------------|-----------------------|-------------------------|
| Rct/Ohm | 16    | 77                    | 73                        | 126                   | 44                      |
| IE      | NA    | 79%                   | 78%                       | 87%                   | 64%                     |

| Label   | 4HC   | [triazole-SH] | [thiadiazole-SH] | [thiazole-SH] | [imidazole-SH] |
|---------|-------|---------------|-------------------|---------------|-----------------|
| Rct/Ohm | 13    | 18            | 19                | 99            | 71              |
| IE      | -23%  | 11%           | 16%               | 84%           | 77%             |

| Label   | H₂SO₄ | [coumarin-S-pyridine] | [coumarin-S-benzimidazole] | [coumarin-S-thiophene] |
|---------|-------|------------------------|------------------------------|-------------------------|
| Rct/Ohm | 16    | 398                    | 133                          | 11                      |
| IE      | NA    | 96%                    | 88%                          | -45%                    |

| Label   | H₂SO₄ | [pyridine-S-pyranone] | [benzimidazole-S-pyranone] | [thiophene-S-pyranone] |
|---------|-------|------------------------|------------------------------|-------------------------|
| Rct/Ohm | 16    | 306                    | 415                          | 229                     |
| IE      | NA    | 95%                    | 96%                          | 93%                     |

| Label   | 4HC   | [2-mercaptopyridine] | [2-mercaptobenzimidazole] |
|---------|-------|-----------------------|-----------------------------|
| Rct/Ohm | 13    | 145                   | 270                         |
| IE      | -23%  | 89%                   | 94%                         |

TABLE 4

Corrosion inhibition efficiency (IE) of the synthesized corrosion inhibitor molecules based on 4-hydroxycoumarin, triacetic acid lactone-based corrosion inhibitors, and separately of the starting materials, in 0.3M hydrochloric acid at 30° C. from EIS testing.

| Label   | HCl | [coumarin-S-triazole] | [coumarin-S-thiadiazole] | [coumarin-S-thiazole] | [coumarin-S-imidazole] |
|---------|-----|------------------------|----------------------------|------------------------|-------------------------|
| Rct/Ohm | 36  | 233                    | 260                        | 259                    | 163                     |
| IE      | NA  | 85%                    | 86%                        | 86%                    | 78%                     |

TABLE 4-continued

Corrosion inhibition efficiency (IE) of the synthesized corrosion inhibitor molecules based on 4-hydroxycoumarin, triacetic acid lactone-based corrosion inhibitors, and separately of the starting materials, in 0.3M hydrochloric acid at 30° C. from EIS testing.

| Label | HCl | (triazole-S-pyrone) | (thiadiazole-S-pyrone) | (thiazole-S-pyrone) | (imidazole-S-pyrone) |
|---|---|---|---|---|---|
| Rct/Ohm | 36 | 179 | 125 | 125 | 98 |
| IE | NA | 80% | 71% | 71% | 63% |

| Label | 4HC | (triazole-SH) | (thiadiazole-SH) | (thiazole-SH) | (imidazole-SH) |
|---|---|---|---|---|---|
| Rct/Ohm | 13 | 44 | 24 | 51 | 68 |
| IE | −23% | 18% | −50% | 29% | 47% |

| Label | HCl | (pyridyl-S-coumarin) | (benzimidazole-S-coumarin) | (thiophene-S-coumarin) |
|---|---|---|---|---|
| Rct/Ohm | 36 | 255 | 162 | 23 |
| IE | NA | 86% | 78% | −57% |

| Label | HCl | (pyridyl-S-pyrone) | (benzimidazole-S-pyrone) | (thiophene-S-pyrone) |
|---|---|---|---|---|
| Rct/Ohm | 36 | 205 | 389 | 141 |
| IE | NA | 82% | 91% | 74% |

| Label | 4HC | (2-mercaptopyridine) | (2-mercaptobenzimidazole) |
|---|---|---|---|
| Rct/Ohm | 13 | 142 | 241 |
| IE | −23% | 75% | 85% |

Figure 7:
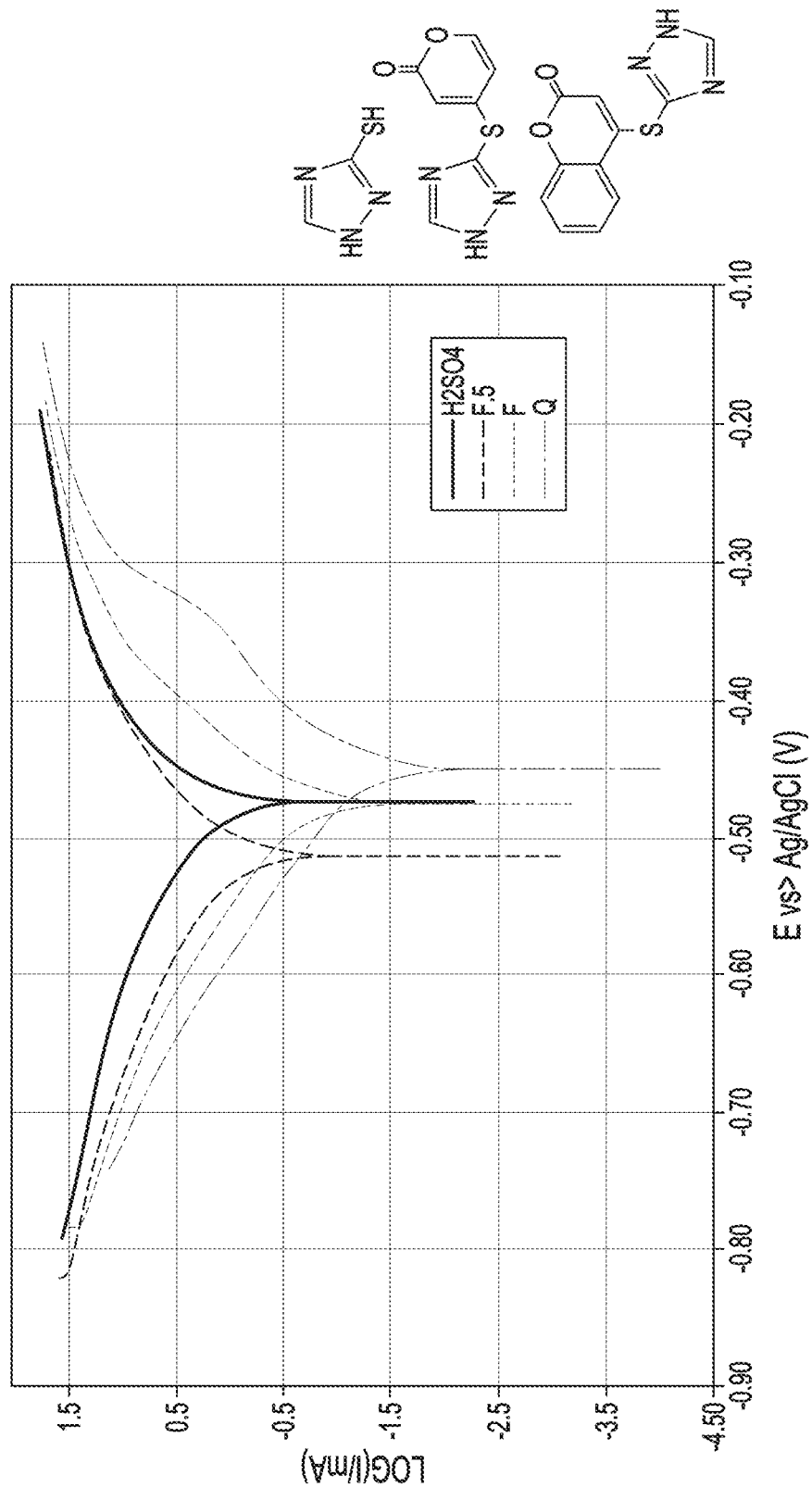
FIG. 7 illustrates polarization curves of various corrosion inhibitors, starting materials thereof, and of $H_2SO_4$.
Figure 8:
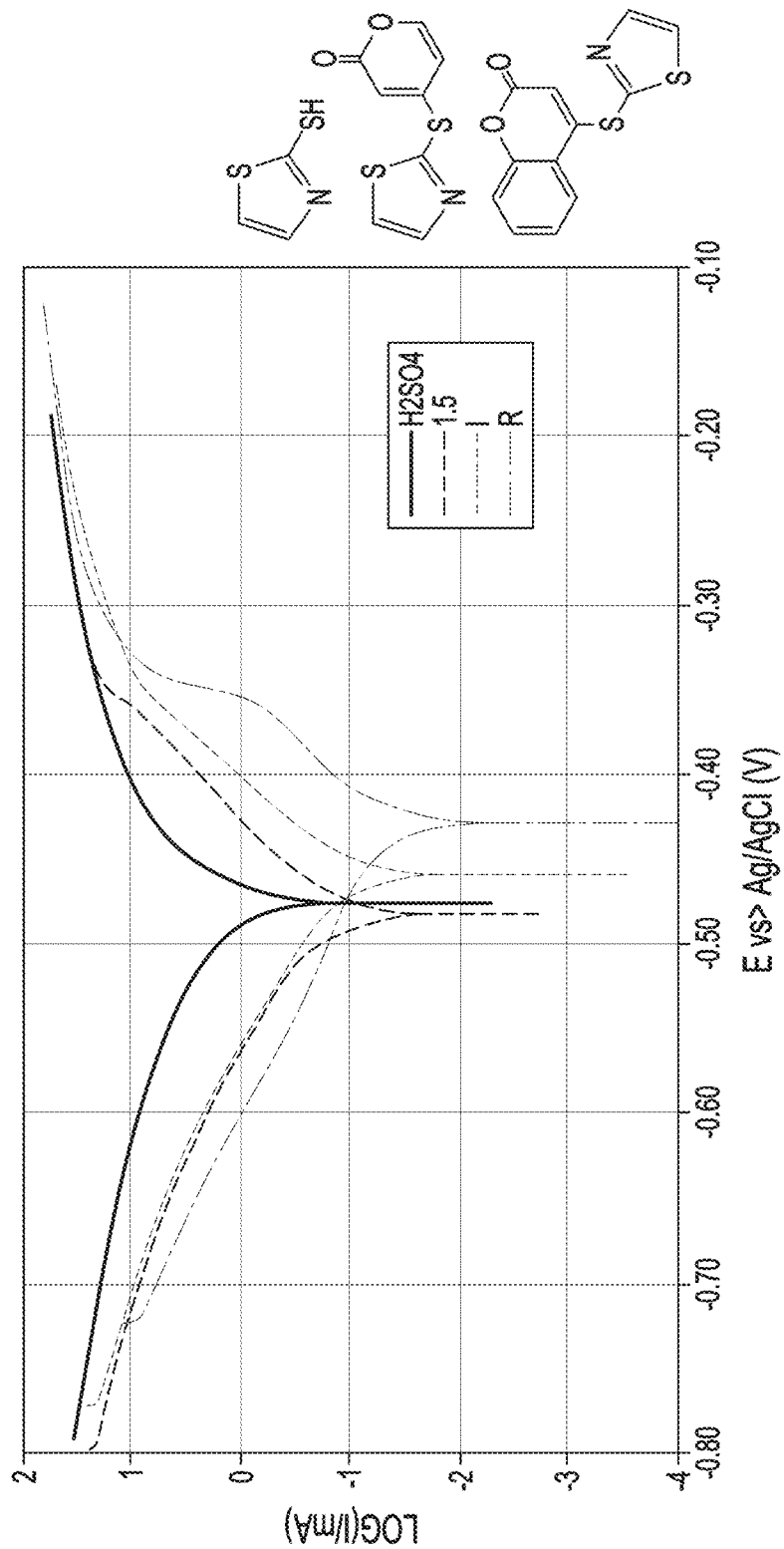
FIG. 8 illustrates polarization curves of various corrosion inhibitors, starting materials thereof, and of $H_2SO_4$.

FIGS. 7-8 illustrate polarization curves of various corrosion inhibitors, starting materials thereof, and of $H_2SO_4$. Lines extending to the left correspond to cathodic hydrogen evolution, and lines extending to the right correspond to anodic iron corrosion.

Overall, we have synthesized novel organic corrosion inhibitors with a good yield and tested with corrosion inhibition performance by EIS. TAL-derived molecules 1, 2, 3, 6, 8, and coumarin-derived molecules 9, 10 showed higher corrosion inhibition efficiency than HTMA in both sulfuric acid and hydrochloric acid.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Exemplary Embodiments

The following exemplary embodiments are provided, the numbering of which is not to be construed as designating levels of importance:

Embodiment 1 provides a heteroaryl-thio-substituted pyrone compound that is a heteroaryl-thio-substituted pyrone or a heteroaryl-thio-substituted coumarin.

Embodiment 2 provides the compound of Embodiment 1, wherein the pyrone or coumarin, other than the heteroaryl-thio substituent, is substituted or unsubstituted.

Embodiment 3 provides the compound of any one of Embodiments 1-2, wherein the pyrone or coumarin is substituted with a single one of the heteroaryl-thio groups.

Embodiment 4 provides the compound of any one of Embodiments 1-3, wherein the pyrone or coumarin is 4-heteroaryl-thio substituted.

Embodiment 5 provides the compound of any one of Embodiments 1-4, wherein the compound is a heteroaryl-thio-substituted pyrone.

Embodiment 6 provides the compound of any one of Embodiments 1-5, wherein the pyrone is 6-methyl substituted and is otherwise unsubstituted other than the heteroaryl-thio substitution.

Embodiment 7 provides the compound of any one of Embodiments 1-6, wherein the coumarin is unsubstituted other than the heteroaryl substitution.

Embodiment 8 provides the compound of any one of Embodiments 1-7, wherein the compound is a 4-heteroaryl-thio-substituted pyrone.

Embodiment 9 provides the compound of any one of Embodiments 1-8, wherein the compound is a 4-heteroaryl-thio-substituted 6-methylpyrone.

Embodiment 10 provides the compound of any one of Embodiments 1-9, wherein the compound is a 4-heteroaryl-thio-substituted coumarin.

Embodiment 11 provides the compound of any one of Embodiments 1-10, wherein the compound is at least 90 wt % pure.

Embodiment 12 provides the compound of any one of Embodiments 1-11, wherein the compound is at least 99 wt % pure.

Embodiment 13 provides the compound of any one of Embodiments 1-12, wherein the heteroaryl-thio substituent is derived from a thiol chosen from:

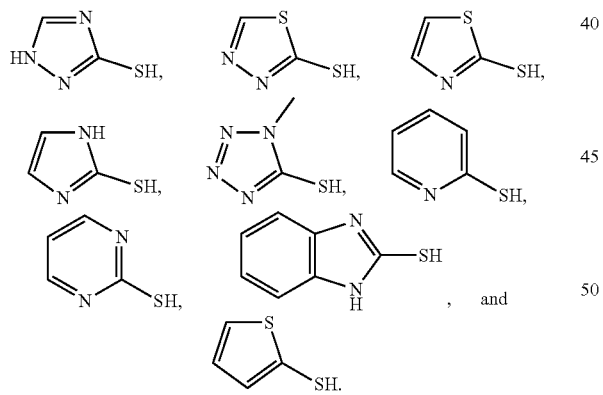

Embodiment 14 provides the compound of any one of Embodiments 1-13, wherein the compound has a structure chosen from:

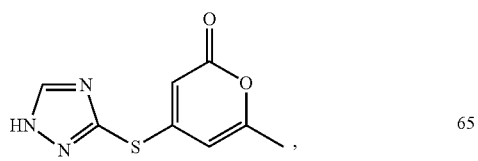

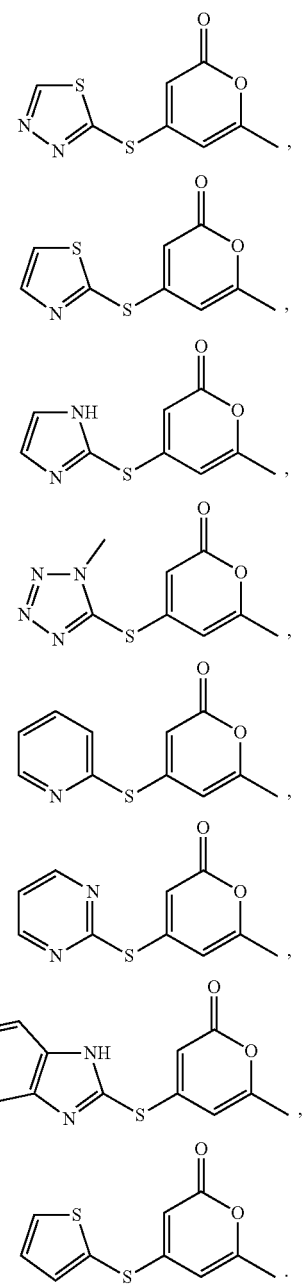

Embodiment 15 provides the compound of any one of Embodiments 1-14, wherein the compound has a structure chosen from:

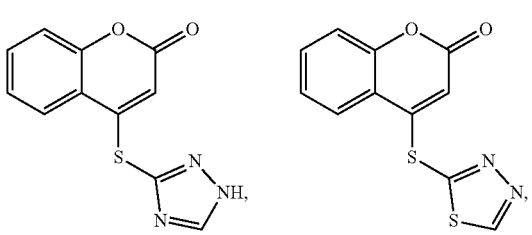

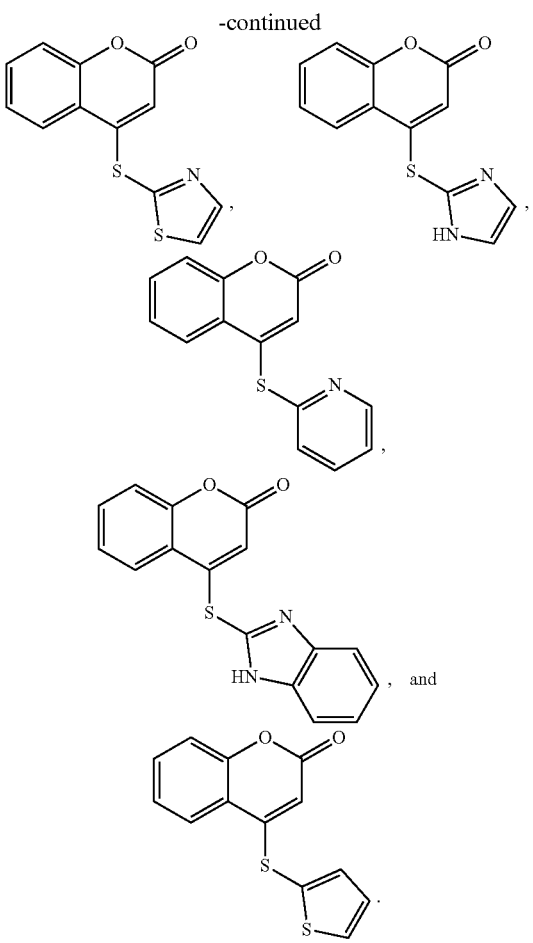

, and

Embodiment 16 provides the compound of any one of Embodiments 1-15, wherein the compound is a corrosion inhibitor of metal.

Embodiment 17 provides the compound of any one of Embodiments 1-16, wherein a reaction product of the compound, an acid, and a metal, is a corrosion inhibitor of the metal.

Embodiment 18 provides the compound of any one of Embodiments 1-17, wherein the compound provides corrosion inhibition of metal when in contract with the metal.

Embodiment 19 provides the compound of any one of Embodiments 1-18, wherein the compound provides corrosion inhibition of metal when in contact with the metal, under acidic conditions.

Embodiment 20 provides the compound of any one of Embodiments 1-19, wherein a metal contacted with the compound under acidic conditions exhibits inhibited corrosion.

Embodiment 21 provides the compound of Embodiment 20, wherein the metal removed from the acidic conditions continues to exhibit inhibited corrosion.

Embodiment 22 provides the compound of any one of Embodiments 1-21, wherein corrosion inhibition of a metal is provided by reaction of the compound with a metal in the presence of an acid.

Embodiment 23 provides the compound of any one of Embodiments 1-22, wherein the compound provides inhibition of biological nitrification.

Embodiment 24 provides the compound of any one of Embodiments 1-23, wherein the compound provides anti-wear properties to a metal.

Embodiment 25 provides a corrosion inhibition composition comprising the compound of any one of Embodiments 1-24, wherein the corrosion inhibition composition inhibits corrosion of a metal.

Embodiment 26 provides the composition of Embodiment 25, wherein the composition is an aqueous composition comprising acid.

Embodiment 27 provides the composition of Embodiment 26, wherein the composition provides inhibited corrosion of the metal during contacting of the composition with the metal.

Embodiment 28 provides the composition of any one of Embodiments 26-27, wherein the composition provides inhibited corrosion of the metal after contacting the composition with the metal.

Embodiment 29 provides the composition of any one of Embodiments 25-28, wherein the composition is a paint, a coating, a spray, a lubricant composition, a metal wear-protection composition, a soil-treatment composition, or a combination thereof.

Embodiment 30 provides a method of inhibiting corrosion, the method comprising:
contacting a metal with the compound of any one of Embodiments 1-24 and/or a reaction product thereof.

Embodiment 31 provides the method of Embodiment 30, wherein the metal is contacted with the compound of any one of Embodiments 1-24 under acidic conditions.

Embodiment 32 provides the method of any one of Embodiments 30-31, wherein the method comprises exposing the metal to an acidic solution comprising the compound of any one of Embodiments 1-24.

Embodiment 33 provides the method of any one of Embodiments 32-32, wherein the method further comprises removing the metal from the acidic solution comprising the compound of any one of Embodiments 1-24.

Embodiment 34 provides the method of Embodiment 33, wherein the method further comprises rinsing residual acidic solution from the metal after removing the metal from the acidic solution.

Embodiment 35 provides the method of any one of Embodiments 31-34, wherein the method provides corrosion inhibition of the metal under the acidic conditions.

Embodiment 36 provides the method of any one of Embodiments 31-35, wherein the method provides corrosion inhibition of the metal after removal from the acidic conditions.

Embodiment 37 provides the method of any one of Embodiments 31-36, wherein the corrosion inhibition comprises corrosion inhibition provided by a reaction product of the compound of any one of Embodiments 1-24 and the acid.

Embodiment 38 provides the method of any one of Embodiments 31-37, wherein the corrosion inhibition comprises corrosion inhibition provided by a reaction product of the compound of any one of Embodiments 1-24, the acid, and the metal.

Embodiment 39 provides the method of any one of Embodiments 30-38, wherein the corrosion inhibition comprises corrosion inhibition provided by a reaction product of any one of Embodiments 1-24.

Embodiment 40 provides the method of any one of Embodiments 30-39, wherein the corrosion inhibition comprises corrosion inhibition provided by a reaction product of the compound of any one of Embodiments 1-24 and the metal.

Embodiment 41 provides the method of any one of Embodiments 30-40, wherein the corrosion inhibition comprises corrosion inhibition provided by the compound of any one of Embodiments 1-24.

Embodiment 42 provides the method of any one of Embodiments 30-41, wherein the metal is a metal comprising aluminum, copper, iron, zinc, an alloy thereof, or a combination thereof. In some embodiments, the metal can be a metal comprising iron or an alloy thereof. In some embodiments, the metal can include manganese, nickel, chromium, molybdenum, boron, titanium, vanadium, tungsten, cobalt, niobium, an alloy thereof, or a combination thereof Embodiment 43 provides the method of any one of Embodiments 30-42, wherein the metal is a steel.

Embodiment 44 provides the method of any one of Embodiments 30-43, wherein the metal is a carbon steel, an alloy steel, or a combination thereof.

Embodiment 45 provides the method of any one of Embodiments 30-44, wherein the metal comprises iron and also comprises manganese, nickel, chromium, molybdenum, boron, titanium, vanadium, tungsten, cobalt, niobium, or a combination thereof.

Embodiment 46 provides a metal having a decreased rate of corrosion, the metal comprising:
a coating and/or adsorbed layer on an exterior surface of the metal comprising the compound of any one of Embodiments 1-24.

Embodiment 47 provides a metal having a decreased rate of corrosion, the metal comprising:
a coating and/or adsorbed layer on an exterior surface of the metal comprising a reaction product of the compound of any one of Embodiments 1-24 and
an acidic solution, or
the exterior surface of the metal, or
a combination thereof.

Embodiment 48 provides a method of forming the compound of any one of Embodiments 1-24, the method comprising:
reacting bromine-substituted pyrone or coumarin with a heteroaryl-thiol to form the heteroaryl-thio-substituted pyrone or heteroaryl-thio-substituted coumarin of any one of Embodiments 1-24.

Embodiment 49 provides the method of Embodiment 48, wherein the pyrone or coumarin used to form the compound of any one of Embodiments 1-24 is naturally derived.

Embodiment 50 provides the compound, composition, or method of any one or any combination of Embodiments 1-49 optionally configured such that all elements or options recited are available to use or select from.

What is claimed is:

1. A heteroaryl-thio-substituted coumarin compound that is a heteroaryl-thio-substituted coumarin, wherein the heteroaryl-thio-substituted coumarin compound has a structure selected from the group consisting of:

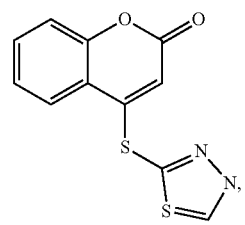 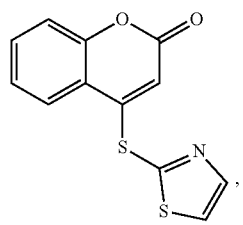

-continued

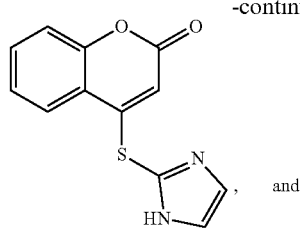 and 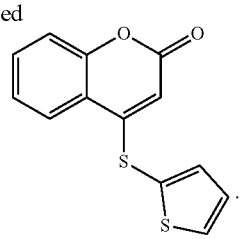

2. The compound of claim 1, wherein the heteroaryl-thio-substituted coumarin compound is at least 90 wt % pure.

3. A corrosion inhibition composition comprising the compound of claim 1, wherein the corrosion inhibition composition inhibits corrosion of a metal.

4. The composition of claim 3, wherein the composition is an aqueous composition comprising acid.

5. A method of forming the compound of claim 1, the method comprising:
reacting bromine-substituted coumarin with a heteroaryl-thiol to form the heteroaryl-thio-substituted heteroaryl-thio-substituted coumarin of claim 1.

6. The compound of claim 1, wherein the heteroaryl-thio-substituted coumarin compound has the structure:

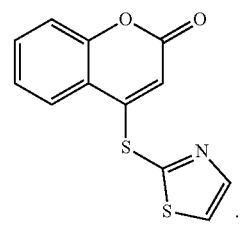 [SMILES: O=c1cc(Sc2nccs2)c2ccccc2o1]

7. The compound of claim 1, wherein the heteroaryl-thio-substituted coumarin compound has the structure:

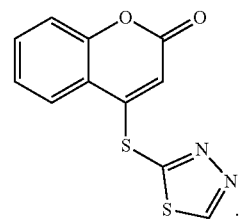 [SMILES: O=c1cc(Sc2nncs2)c2ccccc2o1]

8. The compound of claim 1, wherein the heteroaryl-thio-substituted coumarin compound has the structure:

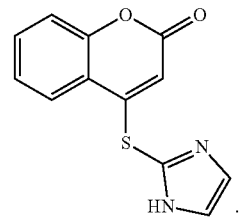 [SMILES: O=c1cc(Sc2ncc[nH]2)c2ccccc2o1]

9. The compound of claim 1, wherein the heteroaryl-thio-substituted coumarin compound has the structure:
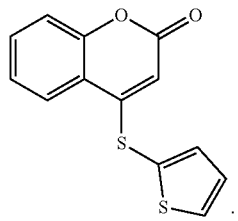
* * * * *

UNITED STATES PATENT AND TRADEMARK OFFICE
CERTIFICATE OF CORRECTION

| | | |
|---|---|---|
| PATENT NO. | : 12,091,602 B2 | Page 1 of 3 |
| APPLICATION NO. | : 17/504307 | |
| DATED | : September 17, 2024 | |
| INVENTOR(S) | : Shanks et al. | |

It is certified that error appears in the above-identified patent and that said Letters Patent is hereby corrected as shown below:

In the Drawings

Sheet 1 of 9, Fig. 1, delete "H2SO4" and insert --$H_2SO_4$-- therefor

On sheet 2 of 9, Fig. 2, delete "HC1" and insert --HCl-- therefor

On sheet 8 of 9, Fig. 7, delete "H2SO4" and insert --$H_2SO_4$-- therefor

On sheet 9 of 9, Fig. 8, delete "H2SO4" and insert --$H_2SO_4$-- therefor

In the Specification

In Column 2, Line 47, delete "6*a-b*" and insert --6A-B-- therefor

In Column 3, Line 10, delete "Y."" and insert --Y,"-- therefor

In Column 3, Line 11, delete "X." and insert --X,-- therefor

In Column 3, Line 13, delete ""an."" and insert --"an,"-- therefor

In Column 3, Line 18, delete ""A." and insert --"A,-- therefor

In Column 3, Line 61, delete "OOR." and insert --OOR,-- therefor

In Column 3, Line 61, delete "CN. $CF_3$." and insert --CN, $CF_3$,-- therefor

In Column 4, Line 22, delete "groups." and insert --groups,-- therefor

Signed and Sealed this
Tenth Day of February, 2026

John A. Squires
*Director of the United States Patent and Trademark Office*

In Column 4, Line 32, delete "N(R)N(R)C(O)OR." and insert --N(R)N(R)C(O)OR,-- therefor In Column 5, Line 65, delete "2-naphthyl)." and insert --2-naphthyl),-- therefor In Column 6, Line 24, delete "2.3-dihydro-benzo[b]thiophenyl." and insert --2.3-dihydro-benzo[b]thiophenyl,-- therefor In Column 7, Line 38, delete "heteroaryl-thio substituted" and insert --heteroaryl-thio-substituted-- therefor In Column 7, Lines 44-45, delete "heteroaryl-thio substituted" and insert --heteroaryl-thio-substituted-- therefor In Column 11, Line 49, delete "heteraryl-thio-substituted" and insert --heteroaryl-thio-substituted-- therefor In Column 12, Line 12, delete "m." and insert --μm.-- therefor In Column 12, Line 54, delete "Na₂ CO₃," and insert --Na₂CO₃,-- therefor In Column 12, Line 66, delete "Litina." and insert --Litina,-- therefor In Column 13, Line 5, delete "mL." and insert --mL,-- therefor In Column 15, Line 19, delete "(t." and insert --(t,-- therefor In Column 15, Line 37, delete "(dd." and insert --(dd,-- therefor In Column 19, Line 8, delete "Ret/Ohm" and insert --Rct/Ohm-- therefor In Column 22, Line 64, delete "(9-10)." and insert --(9-10),-- therefor In Column 23, Line 2, delete "6*a-b*" and insert --6A-B-- therefor In Column 24, Line 3, delete "h." and insert --h,-- therefor In Column 24, in table 3, Line 2, delete "niaterials," and insert --materials,-- therefor In Column 24, in table 3-continued, Line 2, delete "niaterials," and insert --materials,-- therefor In Column 31, Line 46, delete "contract" and insert --contact-- therefor In Column 33, Line 13, after "thereof", insert --.--

CERTIFICATE OF CORRECTION (continued)
U.S. Pat. No. 12,091,602 B2

In the Claims

In Column 34, Lines 24-25, in Claim 5, delete "heteroaryl-thio-substituted heteroaryl-thio-substituted" and insert --heteroaryl-thio-substituted-- therefor